US012656092B2

(12) United States Patent
Ankner

(10) Patent No.: US 12,656,092 B2
(45) Date of Patent: Jun. 16, 2026

(54) BALLISTIC DELIVERY METHOD AND SYSTEM FOR INJECTABLE FORMULATIONS

(71) Applicant: Charles E. Ankner, West Palm Beach, FL (US)

(72) Inventor: Charles E. Ankner, West Palm Beach, FL (US)

( * ) Notice: Subject to any disclaimer, the term of this patent is extended or adjusted under 35 U.S.C. 154(b) by 617 days.

(21) Appl. No.: 17/494,469

(22) Filed: Oct. 5, 2021

(65) Prior Publication Data

US 2022/0120542 A1 Apr. 21, 2022

Related U.S. Application Data

(63) Continuation of application No. 15/243,439, filed on Aug. 22, 2016, now abandoned, which is a continuation-in-part of application No. 14/820,507, filed on Aug. 6, 2015, now Pat. No. 9,585,867.

(51) Int. Cl.

| | |
|---|---|
| *F42B 12/54* | (2006.01) |
| *A61D 7/00* | (2006.01) |
| *A61K 9/00* | (2006.01) |
| *A61K 31/00* | (2006.01) |
| *A61K 45/06* | (2006.01) |
| *A61M 5/20* | (2006.01) |
| *A61M 5/31* | (2006.01) |
| *A61M 5/32* | (2006.01) |
| *A61M 5/46* | (2006.01) |
| *F42B 10/06* | (2006.01) |
| *F42B 10/26* | (2006.01) |

(52) U.S. Cl.
CPC ............... *F42B 12/54* (2013.01); *A61D 7/00* (2013.01); *A61K 9/0019* (2013.01); *A61K 31/658* (2023.05); *A61K 45/06* (2013.01); *A61M 5/20* (2013.01); *A61M 5/2033* (2013.01); *A61M 5/2046* (2013.01); *A61M 5/3295* (2013.01); *A61M 5/46* (2013.01); *F42B 10/06* (2013.01); *F42B 10/26* (2013.01); *A61M 2005/2013* (2013.01); *A61M 2005/206* (2013.01); *A61M 2005/3123* (2013.01)

(58) Field of Classification Search
CPC ......... A61M 2005/14256; A61M 2005/14506; A61M 2005/2013; A61M 2005/206; A61M 2005/3123; A61M 5/142; A61M 5/20; A61M 5/2033; A61M 5/2046; A61M 5/3295; A61M 5/46; F41A 1/00; F41A 21/46; F41C 27/06
See application file for complete search history.

(56) References Cited

U.S. PATENT DOCUMENTS

| | | | |
|---|---|---|---|
| 1,671,364 A | 5/1928 | Gangnes |
| 2,112,758 A | 3/1938 | Blacker |
| 2,348,337 A | 5/1944 | Francis |
| 2,408,252 A | 9/1946 | Ganahl |
| 2,444,283 A | 6/1948 | Detrich |
| 2,699,167 A | 1/1955 | Raiche |
| 2,854,925 A | 10/1958 | Crockford et al. |
| 3,022,785 A | 2/1962 | Crockford et al. |
| 3,037,454 A | 6/1962 | Young |
| 3,207,157 A | 9/1965 | Murdoch |
| 3,209,695 A | 10/1965 | Crockford et al. |
| 3,209,696 A | 10/1965 | Palmer et al. |
| 3,369,660 A | 2/1968 | Hartman |
| 3,386,381 A | 6/1968 | Ferb |
| 3,388,136 A | 6/1968 | Taylor |
| 3,396,660 A | 8/1968 | Bilson et al. |
| 3,429,263 A | 2/1969 | Snyder et al. |
| 3,457,921 A | 7/1969 | Waldeisen |
| 3,502,025 A | 3/1970 | Payne |
| 3,560,528 A | 2/1971 | Petrzilka |
| 3,584,582 A | 6/1971 | Muller |
| 3,616,758 A | 11/1971 | Komarov |
| 3,668,224 A | 6/1972 | Petrzilka |
| 3,690,026 A | 9/1972 | Rose |
| 3,701,533 A | 10/1972 | Palmer |
| 3,715,990 A | 2/1973 | Palmer |
| 3,732,821 A | 5/1973 | Royer |
| 3,734,930 A | 5/1973 | Razan et al. |
| 3,754,509 A | 8/1973 | Gogen |
| 3,763,786 A | 10/1973 | MacDonald |
| 3,776,137 A | 12/1973 | Abbott |
| 3,782,286 A | 1/1974 | Jones et al. |

(Continued)

FOREIGN PATENT DOCUMENTS

| | | | |
|---|---|---|---|
| WO | 1999030764 A1 | 6/1999 | |
| WO | WO1999030764 | * 6/1999 | ............ A61M 25/01 |

OTHER PUBLICATIONS

Shafer, Raymond P., Marihuana, A Signal of Misunderstanding, National Commission on Marihuana and Drug Abuse, 1972, Washington D.C. GPO, USA.

(Continued)

*Primary Examiner* — Audrea B Coniglio

(74) *Attorney, Agent, or Firm* — The Roy Gross Law Firm, LLC; Roy Gross

(57) ABSTRACT

A system and method of humanely dosing a human or animal with a formulation at a distance. A system capable of dosing a recipient with a formulation having a mass between 10 and 500 grains propelled at low-to-medium ballistic velocities (300 to 800 feet per second) and with medium-to-long range ballistic accuracy (10 to over 100 yards) without causing serious physical harm to, nor the death of, the recipient.

16 Claims, 29 Drawing Sheets

(56) References Cited

U.S. PATENT DOCUMENTS

| | | | |
|---|---|---|---|
| 3,820,465 A * | 6/1974 | Delphia | F42B 12/54 |
| | | | 102/512 |
| 3,837,284 A | 9/1974 | Waldeisen | |
| 3,865,038 A | 2/1975 | Barr | |
| 3,893,866 A | 7/1975 | Hollingsworth | |
| 3,901,158 A | 8/1975 | Ferb | |
| 3,911,824 A | 10/1975 | Barr et al. | |
| 3,948,263 A | 4/1976 | Drake, Jr. et al. | |
| 3,951,070 A * | 4/1976 | Flatau | F42B 12/50 |
| | | | 102/502 |
| 3,959,550 A | 5/1976 | Guillod et al. | |
| 3,982,536 A | 9/1976 | Krogseng et al. | |
| 3,987,188 A | 10/1976 | Archer | |
| 3,995,550 A | 12/1976 | D'Amico, Jr. | |
| 4,025,516 A | 5/1977 | Razdan et al. | |
| 4,103,893 A | 8/1978 | Walker | |
| 4,179,517 A | 12/1979 | Mechoulam et al. | |
| 4,262,597 A | 4/1981 | Olson | |
| 4,279,824 A | 7/1981 | McKinney | |
| 4,376,772 A | 3/1983 | Saari et al. | |
| 4,383,530 A | 5/1983 | Bruno | |
| 4,419,936 A | 12/1983 | Coates et al. | |
| 4,449,982 A | 5/1984 | Gould, III | |
| 4,597,580 A | 7/1986 | Gassie | |
| 4,598,096 A | 7/1986 | Grant | |
| 4,664,664 A | 5/1987 | Drake, Jr. | |
| 4,696,347 A | 9/1987 | Stolov et al. | |
| 4,708,065 A | 11/1987 | Schilling et al. | |
| 4,735,612 A | 4/1988 | Chevalier | |
| 4,863,428 A * | 9/1989 | Chevalier | F42B 12/54 |
| | | | 102/512 |
| 4,876,276 A | 10/1989 | Mechouiam et al. | |
| 4,932,329 A | 6/1990 | Logie | |
| 4,976,202 A | 12/1990 | Honigsbaum | |
| 5,014,623 A | 5/1991 | Walker et al. | |
| 5,018,449 A | 5/1991 | Eidson, II | |
| 5,035,183 A | 7/1991 | Luxton | |
| 5,086,703 A | 2/1992 | Klein | |
| 5,202,533 A | 4/1993 | Vandersteen | |
| 5,252,490 A | 10/1993 | ElSohly et al. | |
| 5,284,867 A | 2/1994 | Kloog et al. | |
| 5,338,753 A | 8/1994 | Burstein et al. | |
| 5,356,383 A | 10/1994 | Daly et al. | |
| 5,434,295 A | 7/1995 | Mechouiam et al. | |
| 5,515,785 A | 5/1996 | Zglenicki | |
| 5,521,215 A | 5/1996 | Mechouiam et al. | |
| 5,538,993 A | 7/1996 | Mechouiam et al. | |
| 5,565,649 A | 10/1996 | Tougeron et al. | |
| 5,601,534 A | 2/1997 | Turner | |
| 5,605,928 A | 2/1997 | Mechouiam et al. | |
| 5,618,955 A | 4/1997 | Mechouiam et al. | |
| 5,635,530 A | 6/1997 | Mechoulam et al. | |
| 5,652,407 A | 7/1997 | Carbone | |
| 5,660,865 A | 8/1997 | Pedersen et al. | |
| 5,698,815 A | 12/1997 | Ragner | |
| 5,791,327 A | 8/1998 | Riggs et al. | |
| 5,801,239 A | 9/1998 | Saikia et al. | |
| 5,817,657 A | 10/1998 | Beasley, Jr. et al. | |
| 5,821,450 A | 10/1998 | Fedida | |
| 5,932,610 A | 8/1999 | Shohami et al. | |
| 5,965,839 A | 10/1999 | Vasel et al. | |
| 5,993,423 A * | 11/1999 | Choi | A61M 5/158 |
| | | | 604/155 |
| 6,004,962 A | 12/1999 | Gooberman | |
| 6,077,537 A | 6/2000 | Booth et al. | |
| 6,113,940 A | 9/2000 | Brokke et al. | |
| 6,142,056 A | 11/2000 | Taleyarkhan | |
| 6,143,761 A | 11/2000 | Lochead et al. | |
| 6,213,024 B1 | 4/2001 | Jasper, Jr. et al. | |
| 6,230,630 B1 | 5/2001 | Gibson et al. | |
| 6,262,112 B1 | 7/2001 | Mittendorf et al. | |
| 6,269,747 B1 | 8/2001 | Strandli et al. | |
| 6,284,711 B1 | 9/2001 | Mitch et al. | |
| 6,294,192 B1 | 9/2001 | Patel et al. | |
| 6,302,028 B1 | 10/2001 | Guillot-Ulmann et al. | |

| | | |
|---|---|---|
| 6,328,992 B1 | 12/2001 | Brooke et al. |
| 6,331,560 B1 | 12/2001 | Shohami et al. |
| 6,365,416 B1 | 4/2002 | Elsohly et al. |
| 6,372,768 B2 | 4/2002 | Lowe, III |
| 6,372,799 B1 | 4/2002 | Aberg |
| 6,375,971 B1 | 4/2002 | Hansen |
| 6,393,992 B1 | 5/2002 | Vasel et al. |
| 6,403,126 B1 | 6/2002 | Webster et al. |
| 6,410,588 B1 | 6/2002 | Feldmann et al. |
| 6,425,764 B1 | 7/2002 | Lamson |
| 6,469,054 B1 | 10/2002 | Mittendorf et al. |
| 6,503,532 B1 | 1/2003 | Murty et al. |
| 6,509,005 B1 | 1/2003 | Peart et al. |
| 6,521,630 B1 | 2/2003 | Fliri et al. |
| 6,531,636 B1 | 3/2003 | Mechoulam et al. |
| 6,538,003 B1 | 3/2003 | Galli et al. |
| 6,545,041 B2 | 4/2003 | Shohami et al. |
| 6,545,050 B1 | 4/2003 | Mittendorf et al. |
| 6,566,543 B2 | 5/2003 | Mechoulam et al. |
| 6,569,463 B2 | 5/2003 | Patel et al. |
| 6,573,278 B2 | 6/2003 | Mittendorf et al. |
| 6,584,910 B1 | 7/2003 | Plass |
| 6,615,739 B2 | 9/2003 | Gibson et al. |
| 6,623,730 B1 | 9/2003 | Williams et al. |
| 6,635,237 B2 | 10/2003 | Lowenstein et al. |
| 6,645,747 B1 | 11/2003 | Hallahan et al. |
| 6,713,048 B2 | 3/2004 | Peart et al. |
| 6,720,001 B2 | 4/2004 | Chen et al. |
| 6,727,279 B2 | 4/2004 | Mittendorf et al. |
| 6,730,330 B2 | 5/2004 | Whittle et al. |
| 6,730,519 B2 | 5/2004 | Elsohly et al. |
| 6,734,176 B2 | 5/2004 | Achard et al. |
| 6,736,070 B2 | 5/2004 | Baltos |
| 6,787,530 B1 | 9/2004 | Goodchild et al. |
| 6,807,908 B2 | 10/2004 | Brydes-Price |
| 6,832,604 B1 | 12/2004 | Thompson |
| 6,858,603 B2 | 2/2005 | Achard et al. |
| 6,860,207 B1 | 3/2005 | Robertson |
| 6,864,291 B1 | 3/2005 | Fride et al. |
| 6,878,716 B1 | 4/2005 | Castelhano et al. |
| 6,903,137 B2 | 6/2005 | Fride et al. |
| 6,923,988 B2 | 8/2005 | Patel et al. |
| 6,946,150 B2 | 9/2005 | Whittle |
| 6,949,582 B1 | 9/2005 | Wallace |
| 6,979,689 B2 | 12/2005 | Gonzales et al. |
| 6,997,110 B2 | 2/2006 | Rastegar |
| 7,013,810 B1 | 3/2006 | Brydes-Price |
| 7,025,992 B2 | 4/2006 | Whittle et al. |
| 7,034,013 B2 | 4/2006 | Thompson et al. |
| 7,041,705 B2 | 5/2006 | Mishra et al. |
| 7,081,471 B2 | 7/2006 | Lippa et al. |
| 7,086,337 B2 | 8/2006 | Klein |
| 7,089,863 B1 | 8/2006 | Dindl |
| 7,094,930 B2 | 8/2006 | Quallich et al. |
| 7,194,960 B2 | 3/2007 | Vasel et al. |
| 7,214,716 B2 | 5/2007 | Fride et al. |
| 7,231,875 B2 | 6/2007 | Rastegar |
| 7,234,399 B2 | 6/2007 | Rastegar |
| 7,273,737 B2 | 9/2007 | Hallahan et al. |
| 7,278,358 B2 | 10/2007 | Huffman |
| 7,297,796 B2 | 11/2007 | Dolle et al. |
| 7,325,548 B2 | 2/2008 | Enslin |
| 7,326,735 B2 | 2/2008 | Bell et al. |
| 7,344,736 B2 | 3/2008 | Whittle et al. |
| 7,345,038 B2 | 3/2008 | Bright et al. |
| 7,350,465 B2 | 4/2008 | Keegstra et al. |
| 7,373,887 B2 | 5/2008 | Jackson |
| 7,378,418 B2 | 5/2008 | Yu et al. |
| 7,399,872 B2 | 7/2008 | Webster et al. |
| 7,402,686 B2 | 7/2008 | Duchek |
| 7,426,888 B2 | 9/2008 | Hunt |
| 7,451,707 B1 | 11/2008 | Hadden |
| 7,473,689 B2 | 1/2009 | Feldman et al. |
| 7,526,998 B2 | 5/2009 | Vasel et al. |
| 7,528,127 B2 | 5/2009 | Fledman et al. |
| 7,544,676 B2 | 6/2009 | Dolle et al. |
| 7,581,540 B2 | 9/2009 | Hale et al. |
| 7,597,910 B2 | 10/2009 | McDowell, Jr. |
| 7,621,220 B1 | 11/2009 | Sanford et al. |

(56)                    References Cited

U.S. PATENT DOCUMENTS

| | | |
|---|---|---|
| 7,622,140 B2 | 11/2009 | Whittle et al. |
| 7,648,696 B2 | 1/2010 | McPhillips et al. |
| 7,671,052 B2 | 3/2010 | Dolle et al. |
| 7,681,503 B1 | 3/2010 | Fridley, Jr. et al. |
| 7,690,311 B1 | 4/2010 | Cronemberger |
| 7,690,331 B2 | 4/2010 | Cronemberger |
| 7,700,368 B2 | 4/2010 | Flockhart et al. |
| 7,709,536 B2 | 5/2010 | Whittle |
| 7,727,223 B2 | 6/2010 | Potter et al. |
| 7,743,708 B1 | 6/2010 | Lawrence |
| 7,749,953 B2 | 7/2010 | Bab |
| 7,752,974 B2 | 7/2010 | Wenaas et al. |
| 7,754,680 B2 | 7/2010 | Cunningham et al. |
| 7,759,526 B2 | 7/2010 | Mechouiam et al. |
| 7,766,013 B2 | 8/2010 | Wensley et al. |
| 7,862,543 B2 | 1/2011 | Potter et al. |
| 7,874,253 B2 | 1/2011 | Marx |
| 7,884,133 B2 | 2/2011 | Mechouiam et al. |
| 7,926,424 B1 | 4/2011 | Quintana et al. |
| 7,966,937 B1 | 6/2011 | Jackson |
| 7,968,594 B2 | 6/2011 | Guy et al. |
| 8,020,492 B1 | 9/2011 | Kapeles |
| 8,034,843 B2 | 10/2011 | Whitttle et al. |
| 8,056,480 B2 | 11/2011 | Brydes-Price |
| 8,061,276 B2 | 11/2011 | Danon et al. |
| 8,065,962 B2 | 11/2011 | Haeselich |
| 8,071,641 B2 | 12/2011 | Weiss et al. |
| 8,088,406 B2 | 1/2012 | Potter et al. |
| 8,110,569 B2 | 2/2012 | Putman et al. |
| 8,119,697 B2 | 2/2012 | Mechouiam et al. |
| 8,124,839 B2 | 2/2012 | Park et al. |
| 8,146,505 B2 | 4/2012 | Huffman |
| 8,171,850 B2 | 5/2012 | Hanchett et al. |
| 8,171,853 B2 | 5/2012 | Purvis |
| 8,198,327 B2 | 6/2012 | Mechouiam et al. |
| 8,211,946 B2 | 7/2012 | Whittle |
| 8,227,627 B2 | 7/2012 | Stinchcomb et al. |
| 8,247,609 B2 | 8/2012 | Roques et al. |
| 8,252,973 B2 | 8/2012 | Pojer et al. |
| 8,256,351 B1 | 9/2012 | Kramer et al. |
| 8,278,308 B2 | 10/2012 | Leone-Bay et al. |
| 8,293,211 B2 | 10/2012 | Makriyannis et al. |
| 8,297,187 B2 | 10/2012 | Sullivan |
| 8,314,083 B2 | 11/2012 | Du |
| 8,336,462 B2 | 12/2012 | Danon et al. |
| 8,337,908 B2 | 12/2012 | Letzel et al. |
| 8,342,098 B2 | 1/2013 | Shalev et al. |
| 8,359,978 B2 | 1/2013 | Endicott et al. |
| 8,378,277 B2 | 2/2013 | Sandomirsky et al. |
| 8,389,480 B2 | 3/2013 | Kuliopulos et al. |
| 8,397,641 B1 | 3/2013 | Jackson |
| 8,425,950 B1 | 4/2013 | Santillan et al. |
| 8,425,954 B2 | 4/2013 | Stone |
| 8,438,978 B2 | 5/2013 | Sullivan et al. |
| 8,445,034 B1 | 5/2013 | Coles, Jr. |
| 8,454,945 B2 | 6/2013 | Mccook et al. |
| 8,470,874 B2 | 6/2013 | Musty et al. |
| 8,481,091 B2 | 7/2013 | Ross |
| 8,497,299 B2 | 7/2013 | Mechouiam et al. |
| 8,512,767 B2 | 8/2013 | Ross |
| 8,518,653 B2 | 8/2013 | Takkinen et al. |
| 8,539,885 B2 | 9/2013 | Huffman |
| 8,551,775 B2 | 10/2013 | Vacanti et al. |
| 8,555,875 B2 | 10/2013 | Cook et al. |
| 8,574,188 B2 | 11/2013 | Potter et al. |
| 8,578,919 B2 | 11/2013 | Macy et al. |
| 8,603,515 B2 | 12/2013 | Whittle |
| 8,616,132 B2 | 12/2013 | Drager |
| 8,629,177 B2 | 1/2014 | Castor et al. |
| 8,635,957 B2 | 1/2014 | Orlev et al. |
| 8,642,645 B2 | 2/2014 | Kelly |
| 8,673,368 B2 | 3/2014 | Guy et al. |
| 8,722,938 B2 | 5/2014 | Mechouiam et al. |
| 8,728,544 B1 | 5/2014 | Pritchett |
| 8,771,760 B2 | 7/2014 | Guy et al. |
| 8,778,418 B2 | 7/2014 | Bisterfeld Von Meer |
| 8,794,155 B1 | 8/2014 | Calvert |
| 8,808,734 B2 | 8/2014 | Winnicki |
| 8,846,409 B2 | 9/2014 | Flockhart et al. |
| 8,881,655 B2 | 11/2014 | Aw et al. |
| 8,884,100 B2 | 11/2014 | Page et al. |
| 8,895,061 B2 | 11/2014 | Balwani et al. |
| 8,904,940 B1 | 12/2014 | Pann et al. |
| 8,906,429 B1 | 12/2014 | Kolsky |
| 8,910,630 B2 | 12/2014 | Todd |
| 8,975,245 B2 | 3/2015 | Goodchild et al. |
| 8,980,941 B2 | 3/2015 | Hospodor |
| 8,980,942 B2 | 3/2015 | Stinchcomb et al. |
| 9,016,888 B2 | 4/2015 | Glynn et al. |
| 9,017,737 B2 | 4/2015 | Kikuchi et al. |
| 9,023,322 B2 | 5/2015 | Van Damme et al. |
| 9,034,395 B2 | 5/2015 | Whittle et al. |
| 9,035,130 B2 | 5/2015 | De Meijer |
| 9,044,390 B1 | 6/2015 | Speier |
| 9,066,910 B2 | 6/2015 | Rosenblatt et al. |
| 9,066,920 B2 | 6/2015 | Whalley et al. |
| 9,072,472 B2 | 7/2015 | Potter et al. |
| 9,377,278 B2 | 6/2016 | Rubin |
| 2002/0022667 A1 | 2/2002 | Pace et al. |
| 2002/0031480 A1 | 3/2002 | Peart et al. |
| 2003/0041768 A1 | 3/2003 | Rastegar |
| 2003/0047105 A1 | 3/2003 | Vasel et al. |
| 2003/0106545 A1 | 6/2003 | Verini |
| 2005/0079136 A1 | 4/2005 | Woolfe et al. |
| 2005/0203068 A1 | 9/2005 | Wingard et al. |
| 2007/0038181 A1 | 2/2007 | Melamud et al. |
| 2007/0101891 A1 | 5/2007 | Rastegar |
| 2007/0101892 A1 | 5/2007 | Rastegar |
| 2007/0151551 A1 | 7/2007 | Verini |
| 2008/0112895 A1 | 5/2008 | Kottayil et al. |
| 2009/0030381 A1 | 1/2009 | Lind et al. |
| 2010/0292345 A1 | 11/2010 | Pertwee |
| 2011/0166521 A1 | 7/2011 | Marshall et al. |
| 2012/0022499 A1* | 1/2012 | Anderson ........... A61M 5/2033 604/110 |
| 2012/0211591 A1 | 8/2012 | Sandomirsky et al. |
| 2013/0047481 A1 | 2/2013 | Macy et al. |
| 2013/0059018 A1 | 3/2013 | Parolaro et al. |
| 2013/0089600 A1 | 4/2013 | Winnicki |
| 2013/0303985 A1 | 11/2013 | Wotton et al. |
| 2014/0302148 A1 | 10/2014 | Winnicki |

OTHER PUBLICATIONS

Martin A. Lee, Synthetic Pot as a Milatry Weapon? Meet the Man who Ran the Secret Program, AlterNet, Internet News Service, (http://www.alternet.org/), Jul. 18, 2008, (http://www.alternet.org/story/92049/synthetic_pot_as_a_military_weapon_meet_the_man_who_ran_the_secret_program), Independent Media Institute (IMI) 77 Federal Street—Second Floor San Francisco, CA 94107.

Raffi Khatchadourian, Operation Delirium Decades after a risky Cold War experiment, a scientist lives with secrets., The New Yorker Magazine (http://www.newyorker.com/), Dec. 17, 2012, (http://www.newyorker.com/magazine/2012/12/17/operation-delirium), The New Yorker, 1 World Trade Center, New York, NY 10007.

James S. Ketcum, M.D., Chemical Warfare Secrets Almost Forgotten, A Personal Story of Medical Testing of Army Volunteers with Incapacitating Chemical Agents During the Cold War (1955-1975), 2006-2007, pp. 35-42, ISBN 9781424300808, ChemBooks Inc., Santa Rosa, California 95403 USA.

Joan T. Pickens, Sedative Activity of Cannabis in Relation to Its delta-trans-Tetrahydrocannabinol, British Journal of Pharmacology, (1981), 72, 649-656, 1981, Macmillan Publishers Ltd, The Macmillan Building, 4 Crinan St, London N1 9XW, United Kingdom.

Frederick H. Meyers, M.D., Pharmacology of Marijuana: Just Another Sedative, The Drug Policy Foundation's CME Seminar, Nov. 13, 1992, Washington D.C. (available on October 5, 2106 at: http://druglibrary.org/Schaffer/ library/marij.htm.).

Breathes, William. Denver Westword, LLC. Published Online Jul. 17, 2014; publication verified by WaybackMachine to Mar. 8, 2015.

(56)          References Cited

OTHER PUBLICATIONS

"Dear Stoner: How much THC equals a lethal dose?". Accessed online at Http://web.archive.org/web/20150308183212/http:/westword. com/news/dear-stoner-how-much-thc-equals-a-lethal-dose-512476 on May 31, 2016.

* cited by examiner

BALLISTIC DELIVERY METHOD AND SYSTEM FOR INJECTABLE FORMULATIONS

CROSS REFERENCE TO RELATED APPLICATION

The present application is a continuation of U.S. patent application Ser. No. 15/243,439, filed Aug. 22, 2016, entitled FORMULATION DELIVERY SYSTEM and published as U.S. Patent Application Publication No. 2017/0038184 A1, which is a continuation in part of U.S. application Ser. No. 14/820,507 filed on Aug. 6, 2015 and issued as U.S. Pat. No. 9,585,867, the contents of which are all incorporated herein by reference in their entirety.

FIELD OF THE INVENTION

The present invention is directed to a ballistic injection system for dosing a human or animal with a hypodermic formulation at a distance via the ballistic injection system without causing serious harm to or the death of the recipient.

A Cooperative Classification Code of F42B 12/54 is suggested by the Applicant (Projectiles, missiles for dispensing gases, vapors, powders or chemically reactive substances by implantation, e.g. hypodermic projectiles).

BACKGROUND OF THE INVENTION

It is well known in the fields of non-lethal and less-than-lethal weaponry that humanely rendering a subject (either human or animal) safe to approach and subdue, compliant to commands, and/or to render a subject safe from harm to the subject themselves and/or others; immediately or within moments, saves lives in many critical and life-threatening situations.

Further, if a subject remains safely incapacitated or immobilized for an extended period, such as a period of minutes and/or hours, then taking such a suspect or detainee into lawful custody or containment is safer for both the subduer as well as the subdued and innocent third parties.

In today's complex and dangerous world, Law Enforcement and Correction Officials currently have no way of safely and effectively sedating a suspect or inmate, and consequently Officers often resort to lethal force when threatened or endangered. Sadly, and yet realistically, psychosis and chemical addiction has and does play a lethal role in many such tragic events. Families also suffer for lack of a system and method to sedate safely and quickly a loved one suffering a violent psychosis or chemical intoxication prior to or after summoning emergency medical response and/or Law Enforcement help. Many such emergency events have ended in death after Law Enforcement arrival because family members and concerned others are presented with the tragic dichotomy of having little or no option other than lethal force to stop a loved one from harming themselves or harming others.

Typically, emergency response is will not arrive at an event after notification for minutes to hours, depending upon the location and circumstances. When dealing with a violently psychotic or chemically impaired person, moments and minutes can last eternities for those involved, and horribly often end with deadly result.

Accordingly, providing an effective, instantaneous or near-instantaneous, non-lethal or less-than-lethal, system and method for subduing a subject, such as an already intoxicated, psychotic, extremely agitated, violent or nonviolent detainee, suspected offender, or known offender would be highly advantageous for both the subduer as well as the subject.

Primary goals of both military and civilian Law Enforcement personal are to keep the peace and save innocent lives—including their own lives, those of their "comrades in arms" and those of aggressive or violent subjects in certain circumstances. These goals of both civilian and military Law Enforcement may be better accomplished via the instant invention.

Accordingly, it is an object of the present invention to provide system and method for quickly and safely sedating a subject, thus making subduing, and if required, containing the subject safer for all involved.

Additionally, and depending upon the formulation used, a human or animal may be quickly incapacitated or immobilized at a distance. The purpose of and for incapacitating or immobilizing a human or animal may be many and varied. It is contemplated that the fields of medical science, military combat, law enforcement, corrections, emergency response, mass casualty response, and similar fields of service and endeavor may benefit greatly from known and yet to be developed sedative formulations for medical, scientific, and industrial purposes.

Correspondingly, in the fields of veterinary medical science, zoology, zoo-keeping, animal husbandry, animal control, non-lethal sport hunting, and in many other related fields of endeavor, so-called "tranquilizing" systems, formulations, and methods are well known and widely used. These known systems for medicating and/or sedating an animal primarily function via the explosive release of stored kinetic energy, such as but not limited to compressed gas or compressed-and-expanding spring propulsion systems, and the like, to convey a "tranquilizing dart" to an animal at a distance. Known systems include:

U.S. Pat. No. 7,013,810 to Brydges-Price (herein "Brydges-Price '810" and incorporated in its entirety by reference), discloses and is directed to a projectile for delivery of a tranquilizer; primarily for the delivery of a tranquillizer or medication substance to an animal, the projectile including a cavity to contain such substance, means to deliver the said substance at a point of impact with a target, and means to effectively retard the velocity of the projectile on impact with the target. One stated objective to provide a tranquillizer or other medication delivery system using a projectile, is to be preferably spin stabilized having improved range and accuracy and of an inherently stable ballistic shape. The velocity retarded in such a way as to prevent excess injury or penetration and may be achieved by means which rapidly produces a large increase in area at the nose of the projectile thus spreading and dissipating the kinetic energy over a large area. Referring to PRIOR ART FIG. 1A, the delivery means disclosed and explained in Brydges-Price '810 is as follows: "Located around the needle 4 towards the tip of the nose cap 5 is a gas producing detonator 7 fired by an impact fuse pin 8. In an alternative arrangement two, or more, otherwise inert substances are to be brought together to initiate an action. Attached to the detonator 7 and the needle 4 is the neck 9 of an inflatable bag 10 of which an opposed end 11 is attached to the plug 3. The rear end of the cavity 2 has a piston 12 the rear end of which communicates through concentric passageways 13 around the cavity 2 and ducts 14 in the plug 3 with the interior of the bag 10. The rear end of the casing 1 is closed off by a tail piece 15. In use, and following discharge from the weapon, the needle tip 6 will make initial impact and the detonator 7 is driven back along the needle . . . and fired via the ignition and retention cuff forming a fixed pin assembly 8 to thus inflate the bag 10 rapidly. The bag 10 expands as illustrated . . . and prevents excess penetration whilst spreading the impact energy over a wide area. On inflation of the bag the nose cap 5 is broken open and may be discarded. In an alternative arrangement the nose cap 5 may spread open as shown in a petaline manner and add to the retardation effect. The bag may be striated longitudinally or laterally and coated or impregnated with gas producing chemical compounds to both accelerate expansion and strengthen the bag membrane. The bag inflation gas bleeds through ducts 14 and passageways 13 to drive piston 12 forward thus delivering the drug through the needle 6. The nose part of the projectile may include a solid foam-like or gel-like substance forming an impact absorbing material which spreads on impact. More specifically the gel may comprise a nanoporous open cell foam of the kind known by the trade mark Aerogel. The projectile has a particular use for soft skin animals which presently require firing at close range typically 20 m. A smaller dart construction may be applied to birds and reptiles."

U.S. Pat. No. 6,807,908 to Brydges-Price (herein "Brydges-Price '908" and incorporated in its entirety by reference), discloses and is directed to " . . . a projectile including means to effectively retard the velocity of the projectile on impact with a target wherein the velocity is retarded in such a way as to prevent excess injury or penetration by deployment of means, following impact with a target, which rapidly expands to produce a large increase in the area at the nose of the projectile to spread the kinetic energy over a large area, characterized in that said expansion of said means is effected using a pressurized gaseous medium carried in the projectile. Preferably the velocity retarding means comprises an inflatable membrane which is subject to the pressurized medium through means actuated on impact with a target, for example by a impact sensor or by means of a proximity sensing means, or by physical displacement actuating a valve device, the membrane being inflated using said pressure, preferably being gas pressure, stored in the projectile and preferably derived from the propulsive charge gases occurring on firing the projectile from a weapon." A further stated alternative object of Brydges-Price '908 is: " . . . to provide a non-lethal projectile which may be fired with accuracy at a soft target directly and even at close ranges and which is designed not to penetrate to any significant extent and which should only cause minimal injury to the limbs or torso. Preferably the velocity retarding means comprises an inflatable membrane which is subject to the pressurized medium through means actuated on impact with a target, for example by a impact sensor or by means of a proximity sensing means, or by physical displacement actuating a valve device, the membrane being inflated using said pressure, preferably being gas pressure, stored in the projectile and preferably derived from the propulsive charge gases occurring on firing the projectile from a weapon.". Referring to PRIOR ART FIG. 1B, " . . . On impact with a target the nose plug 9 is moved back over the needle 5 exposing the orifice 6 to permit some substance 3 in the cavity 2 to bleed thus allowing piston 4 to move forward. This movement uncovers apertures 16 in the wall of compartment 2 and permits stored gas pressure in compartment 15 to enter the cavity between casing 1 and compartment 2. This compartment connects through passageways with the cavity 17 inside the membrane 7 and thus rapidly inflates same. Where the membrane is of rubber it will stretch and expand. The membrane could be of a nonor partly-stretchable material which is folded into the nose cone. During this action the nose 8 is split open and is discarded or peels back."

U.S. Pat. No. 6,736,070 to Baltos (herein "Baltos" and incorporated in its entirety by reference), discloses and is directed to " . . . a so-called "collapsule" bullet, which is a molded, hollow cavity that is filled with a tranquilizing fluid. Preferably, the "collapsule" is fabricated using a high-strength malleable plastic polymer. The bullet is fitted with a so-called "injectile," which is a hypodermic injection spike (to transmit the tranquilizing fluid) that is backed and driven by an inertia base mass (i.e., lead core) located at the base of the bullet. Note that the term "Collapsule™" is a derivative of the terms "collapse" and "capsule," while the term "Injectile™" is a derivative of the terms "injection" and "projectile." In addition to those terms and addressing the function of the dynamic inertia base to shed mass in the form of a liquid and/or a secondary means of incapacitation the applicant also seeks recognition of the term "Fluid Activated Repulsive Trauma™" (F.A.R.T.™).". Referring to PRIOR ART FIG. 1C, "Specifically, the bullet casing is designed to collapse into the form of a flange or "mushroom" upon impact, creating a tendency for the bullet's kinetic energy to be distributed radially and uniformly to the target's body. This uniform and radial distribution of energy, along with the energy transfer that occurs upon impact and delivery of the tranquilizer fluid simply lacks sufficient energy to penetrate further. This makes the device safer for use in confined spaces (e.g., aircraft compartments) where innocent bystanders may be hit. In addition, the collapsule bullet does not deliver a massive blow that might destroy body tissue (as would a conventional bullet). Instead, it contributes to "shock-trauma disorientation and distraction," making the target easier to stop or subdue. This "shock trauma" will also accelerate the effectiveness of the tranquilizer fluid due to the heart rate increase that occurs naturally after learning one has just been shot."

U.S. Pat. No. 3,820,465 to Delphia (herein "Delphia" and incorporated in its entirety by reference), discloses and is directed to " . . . provide a sedative bullet which includes an outer casing member, a least a portion of which is collapsible; a fluid carrying vessel supported within the case member, the vessel including a fluid injection means; fluid means disposed within the casing member for movement in response to the collapse of the collapsible portion, and discharge means for contacting with the moving fluid means for discharging the vessel.". Referring to PRIOR ART FIG. 1D, "When the bullet 10 is fired and strikes an object, the nose portion 14 collapse and the needle 28 is driven into a target 42 through the guide member 38 . . . The collapsing of the nose portion 14 simultaneously forces the heavy fluid 36 toward the rear of the casing 12 and the resulting pressure forces the piston member 32 forwardly. The forward motion of a piston member 32 forces the sedative fluid out of the vessel 24 and discharges it into the target 42 though the needle 28."

U.S. Pat. No. 3,584,582 to Muller (herein "Muller" and incorporated in its entirety by reference), discloses and is directed to " . . . improvements to cartridges used in paralyzing men or animals and its main objective is to project such cartridges from a gun or the like forcibly discharging therefrom a hypodermic fluid into the target upon impact." Muller further discloses " . . . a casing which houses a detonating charge and of a bullet body inserted thereto having a outer hollow portion made of ductile material such as plastic, zinc, lead, rubber or the like to be compressed upon reaching a target. An upstanding hypodermic needle and a hypodermic medium are arranged within said hollow bullet body and upon impact upon a target the needle penetrates through the wall thereof into the target and carries hypodermic medium thereto.". Referring to PRIOR ART FIG. 1E, "The bullet 11 is a closed hollow body which at least in its outer part 11a is made of compressibly deformable ductile material such as plastic, zinc, lead, rubber or the like. At the base of the hollow bullet 11 is a deformable, for example a plastic sack or similar container 13 which is filled with an and is communicatingly topped by baseplate 15 of an upstanding hypodermic needle 14 contacting with its end in the inner wall of the hollow bullet. A compression ring 16 or the like rests upon the needle plate 15. After the cartridge has been fired, the bullet 11 impinges on the target the upper part of the starts to be compressed . . . and the needle 14 penetrates through the wall of the hollow bullet portion 11a into the target. Upon further compression the ring 16 compresses the sack 13 and forces the anesthetic therefrom through the needle 14 into the target."

All such known systems, however, have many disadvantages, including but not limited to: short effective range—typically less than 10 to 25 yards, limited total formulation volume—typically 1 to 5 mL, limited accuracy—typically caused by poor stabilization, low or no induced ballistic spiral, and/or low ballistic velocities. Consequently, such systems are not well suited for emergency or immediate use situations; nor specifically suited for use in sedating a human at a distance.

Such known delivery systems must be "prepped" minutes or hours before use—and once ready for use must be deployed within minutes or hours; thus making such systems unsuited and ineffective for routine emergency deployment, especially for use with human recipients.

Primarily and most disadvantageously, all such known and so called "dart and dart systems" or "sedative bullets" utilize a single hypodermic needle configured centrally along the longitudinal axis of a projectile. Such configurations inherently limit the operational velocity of the hypodermic projectile and require a method of either retarding overall muzzle velocity, retarding projectile velocity during flight, or by dissipating, redirecting, or cushioning the imparted energy of the projectile upon target impact; all required to facilitate safe and effective hypodermic dosing with a single and central needle while not permanently injuring or killing the recipient.

Other known non-hypodermic, non-lethal or less-than-lethal impact type weapons and techniques include but are not limited to so-called rubber, wax, or plastic bullets, "bean-bag" bullets, airfoil projectiles, and the like. However, even these devices if poorly designed and/or carelessly deployed may cause unintended serious injury to and/or the death of a recipient. Known systems utilizing chemical explosive or charge propulsion (that is "gun-powder" or "black-powder") based deliver systems, due to the inherent dangers to life and limb from a solid or semi-solid ballistic projectile impacting a living organism at moderate to high velocities, can and do cause serious injury and/or death when deployed.

Accordingly, and consequently, such known systems propel projectiles at relatively low ballistic velocities, typically less than 300 feet per second (FPS), making such systems less than effective at medium to long ranges, and also less than effective in emergency yet routine circumstances.

However, world-wide commercially available non-lethal kinetic impact-based weapon systems may be used to fire or propel a ballistic hypodermic projectile. Well known types include, but are not limited to, 40 mm and/or 12 gauge "shot-shell" based systems utilizing rubber, plastic, beanbag, or other similar kinetic impact projectiles. Such known systems may easily be utilized with the instant inventive delivery system to dose a recipient with a formulation at a distance.

The widely known "use of force continuum" outlines a specific progression of force, used and adhered to by many Law Enforcement and Corrections agencies. The use of force continuum varies considerably among different departments and jurisdictions, and especially varies related to the wide gap between empty hand control and deadly force techniques. One example of a general use of force continuum model cited in many U.S. government publications is as follows:

1. Officer presence—the professionalism, uniform, and utility belt of the Law Enforcement Officer and the marked vessel or vehicle the Officer arrives in. The visual presence of authority is normally enough for a subject to comply with an Officer's lawful demands. Depending on the totality of the circumstances, a call/situation may require additional Officers or on scene Officers may request assistance in order to gain better control of the situation and ensure a safer environment for all involved. It also will depend on the circumstances of the situation. For example, depending on how many people are at the scene with the Officer, a larger presence may be required. However, if ten Officers arrive at a scene with only a single suspect, the public may perceive the situation as an excessive use of Officer presence within the use of force continuum. In many models, Officer presence includes the Officer's personal defense weapon or firearm unholstered and pointed at a subject.

2. Verbal commands/cooperative controls—clear and understandable verbal direction by an Officer aimed at the subject. In some cases, it is necessary for the Officer to include a consequence to the verbal direction so that the subject understands what will happen if the subject refuses to comply with the Officer's direction. The verbal command and the consequence must be legal and not considered excessive according to the continuum. For example, an Officer could not order a disabled person in a wheelchair to stand up or be sprayed by oleoresin capsicum (OC) pepper spray.

3. Empty-hand submission techniques, PPCT—Pressure Point Control Tactics, Control Tactics, Techniques—a level of force that has a low probability of causing soft connective tissue damage or bone fractures. This would include joint manipulation techniques, applying pressure to pressure points, and normal application of handcuffs.

4. Hard control techniques/Aggressive response techniques—the amount of force that has a probability of causing soft connective tissue damage, bone fractures, or irritation of the skin, eyes, and mucus membranes. This would include kicks, punches, stuns and use of aerosol sprays such as oleoresin capsicum (OC) pepper spray. Some models split these techniques between empty hand, soft control, and intermediate weapon techniques.

5. Intermediate weapons—an amount of force that would have a high probability of causing soft connective tissue damage or bone fractures. (e.g. expandable baton, baton, taser, beanbag rounds, rubber fin stabilized ammunition, mace, police dogs, etc.). Intermediate weapon techniques are designed to impact muscles, arms and legs, and intentionally using an intermediate weapon on the head, neck, groin, kneecaps, or spine would be classified as deadly or lethal force.

6. Lethal force/Deadly force—a force with a high probability of causing death or serious bodily injury. Serious bodily injury includes protracted or obvious physical disfigurement, or protracted loss of or impairment to the function of a bodily member, organ, or the mental faculty. A firearm is the most widely recognized lethal or deadly force weapon, however, an automobile or weapon of opportunity (knife, club, heavy object) could also be defined as a deadly force utility.

In view of the limits of the use of force continuum techniques, it is desirable to provide a system and method to provide a delivery system for incapacitating a recipient with a medicative and/or sedative formulation at a distance.

It is further desirable to provide a hypodermic projectile with which a recipient may be dosed with a medicative and/or sedative formulation at a distance without causing permanent serious injury to or the death of the recipient.

It is further desirable to provide a system and method of providing a sedative formulation and delivery system free of preparatory steps prior to use.

It is further desirable to provide a system and method of providing a sedative formulation which remains safe and effective over a long time period, and under adverse environmental extremes such as but not limited to: temperature, humidity, shock, vibration, ballistic g-force, instantaneous acceleration, instantaneous deceleration, wind blast, and the like.

It is further desirable to provide a system and method of providing a sedative formulation and delivery system which remains operant over a long time period, and under adverse environmental extremes such as but not limited to: temperature, humidity, shock, vibration, ballistic g-force, instantaneous acceleration, instantaneous deceleration, wind blast, and the like.

SUMMARY OF THE INVENTION

It is therefore an object of the present invention is to provide a system and method for inducing a dose of a formulation in a recipient at or from a distance.

Another object of the present invention is to provide a ballistic hypodermic projectile with which a recipient may be dosed with a formulation at a distance without causing permanent serious injury to or the death of the recipient.

Another object of the present invention is to provide a delivery system free of preparatory steps prior to use in routine yet emergency situations.

Another object of the present invention is to provide a system for formulation delivery which remains effective and ready for use over a long time period, and under adverse environmental extremes such as but not limited to: temperature, humidity, shock, vibration, ballistic g-force, instantaneous acceleration, instantaneous deceleration, wind blast, and the like.

Another object of the present invention is to provide a formulation delivery system which remains operant over a long time period, and under adverse environmental extremes such as but not limited to: temperature, humidity, shock, vibration, ballistic g-force, instantaneous acceleration, instantaneous deceleration, wind blast, and the like.

These and other objects of the invention are achieved by providing a projectile injection system for dosing a human or animal recipient from a distance, the system comprising: a housing having a longitudinal axis, a distal end, and a proximal end, wherein said housing has at least one cavity storing a hypodermic formulation and at least one outlet port through which the hypodermic formulation exits said housing; and an injector head having at least one inlet port fluidly connected to the at least one outlet port of the housing, and at least one distal hypodermic needle extending distally from the injector head, the injector head mounted to the distal end of the housing via a rotatable hub, wherein upon contact with the recipient, the at least one distal hypodermic needle penetrates the recipient and the hypodermic formulation exits the at least one cavity and passes through the at least one outlet port of the housing into the at least one inlet port of the injector head and through the at least one distal hypodermic needle, so that the recipient is dosed with the hypodermic formulation without causing serious injury to or the death of the recipient.

It is an object of the instant invention to provide a spiraling ballistic flight projectile injection system for dosing a human or animal recipient with a formulation via injection at a ballistic distance, the system comprising: a housing having a longitudinal axis, a distal end, and a proximal end, wherein said housing has at least one cavity storing the formulation and at least one distal outlet port through which the formulation exits said housing; an injector head having a distal end, a proximal end, and a longitudinal axis in common with the housing longitudinal axis, including at least one proximal inlet port fluidly connected to the at least one distal outlet port of the housing, and including at least one curved distal hypodermic needle extending distally from the injector head offset from the housing and injector head longitudinal axis, the injector head proximal end mounted to the housing distal end along the housing and injector head longitudinal axis via a rotatable hub, the rotatable hub configured to allow the injector head to spin along the common longitudinal axis in respect to the housing, and wherein upon spiraling ballistic contact with the recipient, the at least one curved distal hypodermic needle, cooperatively with the direction of rotation of the housing and injector head along the common longitudinal axis of the housing and injector head, penetrates the dermis of the recipient to a depth facilitative of and suitable for subdermal bolus injection of the formulation, wherein the injector head when impacting the recipient constructively stops both distal and rotational movement along the common longitudinal axis, wherein the formulation exits the at least one cavity and passes through the at least one distal outlet port of the housing into the at least one proximal inlet port of the injector head and through the at least one curved distal hypodermic needle, so that the recipient is injected with the formulation without causing serious injury to or the death of the recipient.

It is an object of the instant invention to provide a spiraling ballistic flight projectile injection system for dosing a human or animal recipient with a formulation via injection at a ballistic distance wherein formulation is a sedative.

It is an object of the instant invention to provide a spiraling ballistic flight projectile injection system for dosing a human or animal recipient with a formulation via injection at a ballistic distance, wherein said projectile injection system is propelled by the group consisting of single-shot, semi-automatic, or fully automatic revolvers, pistols, shotguns, scatterguns, rifles, and combinations thereof.

It is an object of the instant invention to provide a spiraling ballistic flight projectile injection system for dosing a human or animal recipient with a formulation via injection at a ballistic distance, wherein the housing further includes a plunger and a housing vent, wherein the housing vent allows for housing pressure equalization when and as the plunger displaces resulting in the injection of the formulation into the recipient.

It is an object of the instant invention to provide a spiraling ballistic flight projectile injection system for dosing a human or animal recipient with a formulation via injection at a ballistic distance, wherein the injection system comprises a turbine or worm gear in communication with the rotatable hub, wherein when the housing continues rotation as the injector head remains constructively stationary, the turbine or worm gear forces the formulation through the at least one outlet port resulting in the injection of the formulation into the recipient.

It is an object of the instant invention to provide a spiraling ballistic flight projectile injection system for dosing a human or animal recipient with a formulation via injection at a ballistic distance, wherein the system is reusable.

It is an object of the instant invention to provide a spiraling ballistic flight projectile injection system for dosing a human or animal recipient with a formulation via injection at a ballistic distance, wherein the injector system utilizes inertial forces upon impact of the injector head with the recipient resulting in the injection of the formulation into the recipient.

It is an object of the instant invention to provide a spiraling ballistic flight projectile injection system for dosing a human or animal recipient with a formulation via injection at a ballistic distance, wherein the housing further includes a worm gear along the common longitudinal axis in communication with the plunger and in communication with the rotatable hub, whereby the continuing rotation of the housing along the common longitudinal axis in relation to the hypodermic injector head and after impact with the recipient causes the plunger to displace along the common longitudinal axis resulting in the injection of the formulation.

It is an object of the instant invention to provide a spiraling ballistic flight projectile injection system for dosing a human or animal recipient with a formulation via injection at a ballistic distance, wherein the housing further includes a gas under pressure, wherein when the gas is suddenly released, or comprises an explosive substance whereby when ignited expands, or comprises a spring under compression whereby when suddenly released, causes the plunger to displace resulting in the injection of the formulation.

It is an object of the instant invention to provide a spiraling ballistic flight projectile injection system for dosing a human or animal recipient with a formulation via injection at a ballistic distance, wherein the at least one hypodermic needle further includes a barb.

It is an object of the instant invention to provide a spiraling ballistic flight projectile injection system for dosing a human or animal recipient with a formulation via injection at a ballistic distance, wherein the at least one hypodermic needle is configured in an arc.

It is an object of the instant invention to provide a spiraling ballistic flight projectile injection system for dosing a human or animal recipient with a formulation via injection at a ballistic distance, wherein the at least one hypodermic needle is configured in one or more cycloidal, epicycloidal, hypocycloidal, or other spiral arc.

It is an object of the instant invention to provide a spiraling ballistic flight projectile injection system for dosing a human or animal recipient with a formulation via injection at a ballistic distance, wherein the injector head further comprises at least one cooperative strut corresponding to the at least one hypodermic needle and configured in such a manner as to facilitate dermal penetration of the recipient by the at least one hypodermic needle and to facilitate the injection of the formulation into the recipient.

It is an object of the instant invention to provide a spiraling ballistic flight projectile injection system for dosing a human or animal recipient with a formulation via injection at a ballistic distance, wherein the outer circumference of the projectile injection system changes during ballistic flight.

It is an object of the instant invention to provide a spiraling ballistic flight projectile injection system for dosing a human or animal recipient with a formulation via injection at a ballistic distance, wherein the outer circumference of the projectile injection system changes after impacting the recipient.

It is an object of the instant invention to provide a spiraling ballistic flight projectile injection system for dosing a human or animal recipient with a formulation via injection at a ballistic distance, wherein the rotatable hub further includes or operates as a clutch between the housing and the injector head.

It is an object of the instant invention to provide a spiraling ballistic flight projectile injection system for dosing a human or animal recipient with a formulation via injection at a ballistic distance, wherein the injector head further includes an airfoil.

It is an object of the instant invention to provide a spiraling ballistic flight projectile injection system for dosing a human or animal recipient with a formulation via injection at a ballistic distance, wherein the ballistic distance is a short-range ballistic distance of less than 10 yards.

It is an object of the instant invention to provide a spiraling ballistic flight projectile injection system for dosing a human or animal recipient with a formulation via injection at a ballistic distance, wherein the ballistic distance is a medium-to-long range ballistic distance of 10 to 100 yards.

It is an object of the instant invention to provide a spiraling ballistic flight projectile injection system for dosing a human or animal recipient with a formulation via injection at a ballistic distance, wherein the ballistic distance is a long-range ballistic distance of greater than 100 yards.

It is an object of the instant invention to provide a method for injecting a human or animal at a ballistic distance with a formulation, the method comprising the steps of: providing a ballistic flight injection projectile including a housing, the housing including at least one outlet port and a formulation, and an injector head including at least one inlet port and at least one hypodermic needle, and a rotational hub, wherein the injector head is mounted to the housing via the rotational hub, the rotational hub configured to allow the injector head to spin with respect to the housing; and propelling the ballistic flight injection projectile in a spiraling ballistic trajectory to impact a recipient, wherein upon or after the injector head impacts the recipient, the recipient is injected with the formulation without causing serious injury to or the death of the recipient resulting from the injector head impacting the recipient or the injecting of the formulation.

It is an object of the instant invention to provide a method for injecting a human or animal at a ballistic distance with a formulation, wherein when the spiraling injector head impacts the recipient, the at least one hypodermic needle cooperatively with the direction of rotation penetrates the derma of the recipient to a depth facilitative of and suitable for subdermal bolus injection of the formulation without causing serious injury to or the death of the recipient due to the rotational hub allowing the housing to continue rotation and thus dissipating the remaining kinetic energy after the injector head has stopped rotation.

It is an object of the instant invention to provide a method for injecting a human or animal at a ballistic distance with a formulation wherein the spiraling injection projectile is propelled by the group consisting of single-shot, semi-automatic, or fully automatic revolvers, pistols, shotguns, scatterguns, rifles, and combinations thereof.

These and other objects of the invention are achieved by the claims.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1A:
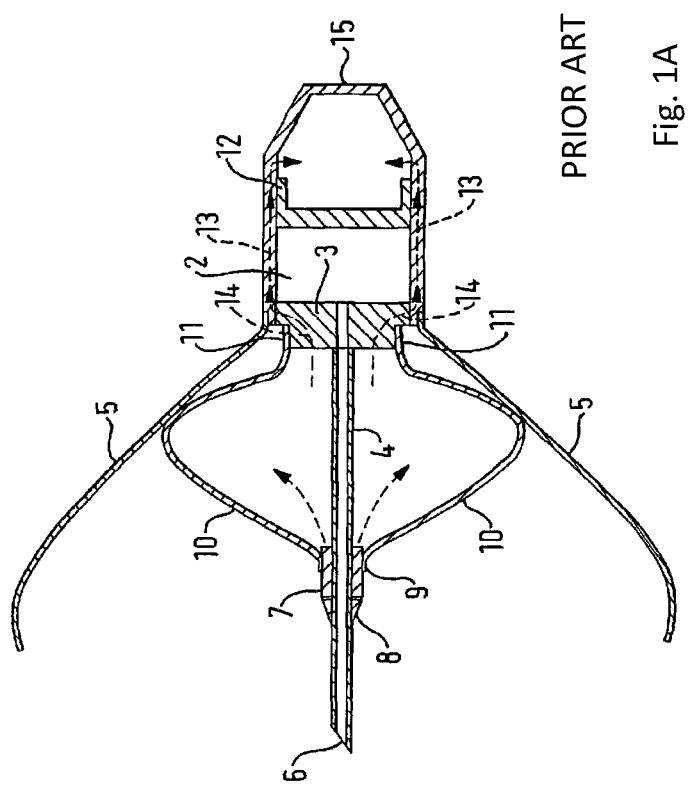
FIGS. 1A-1E are schematic diagrams of various PRIOR ART delivery systems.
Figure 1B:
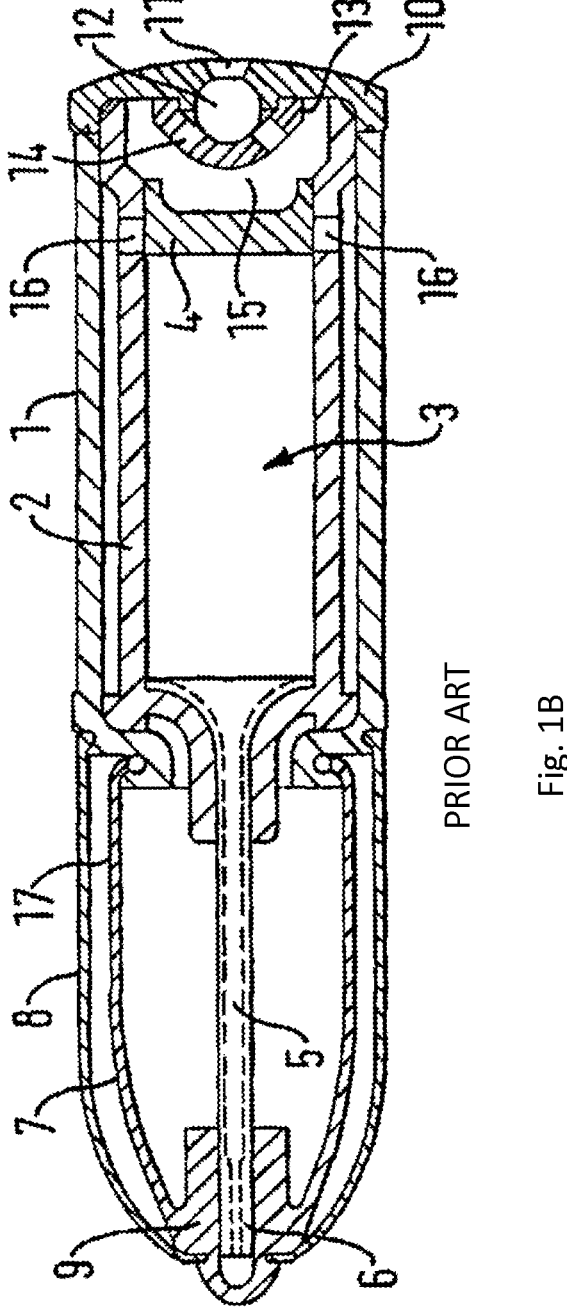
Figure 1C:
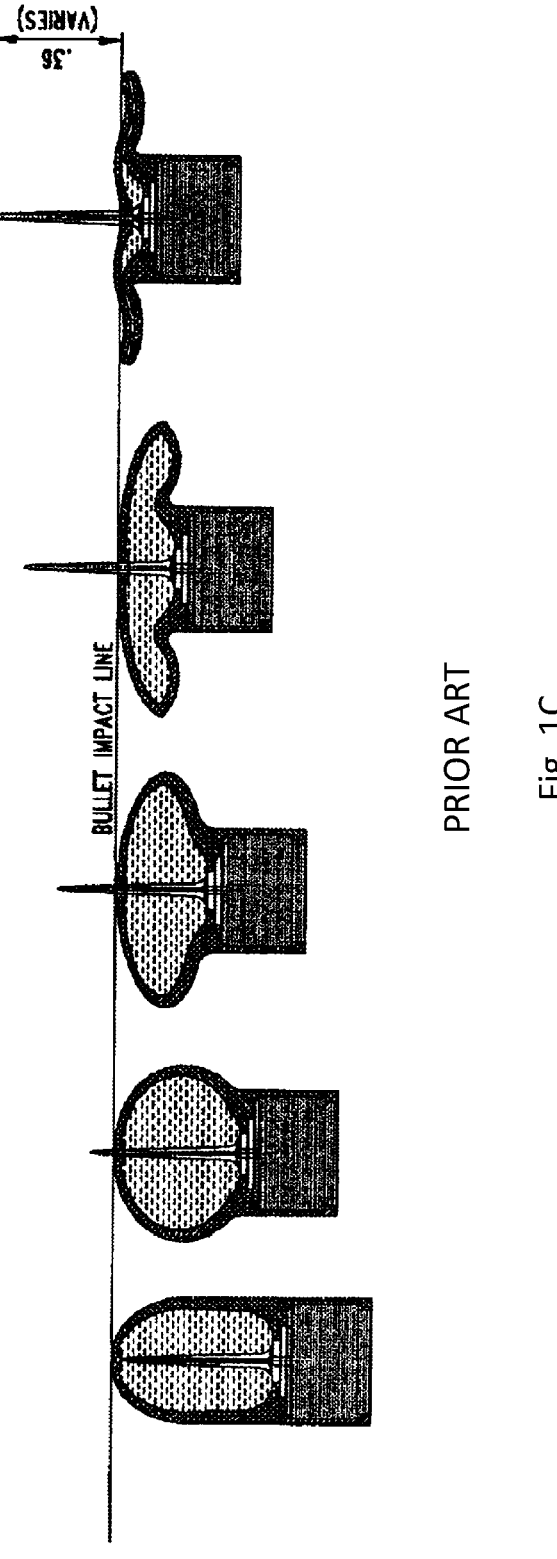
Figure 1D:
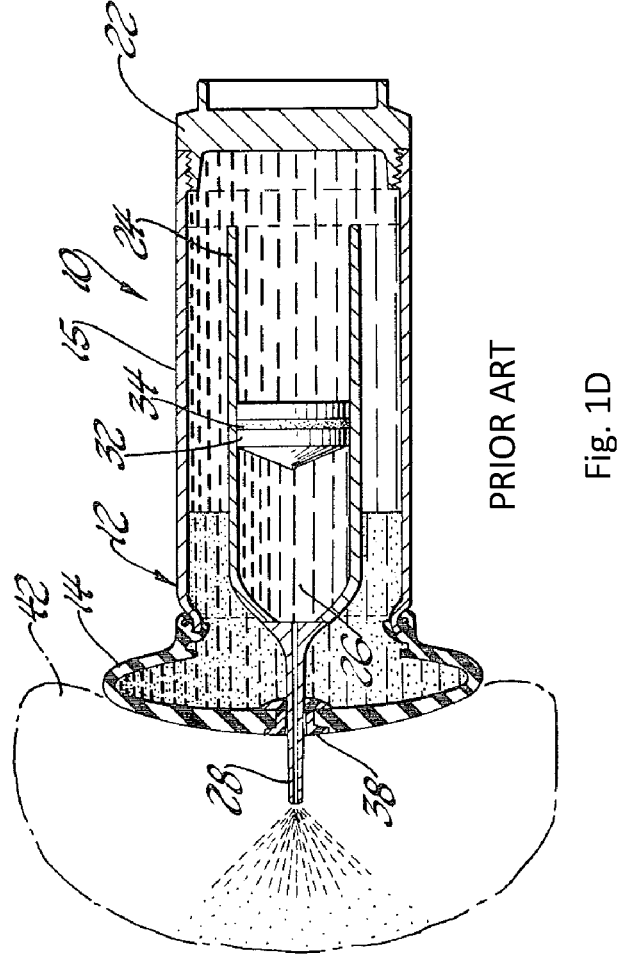
Figure 1E:
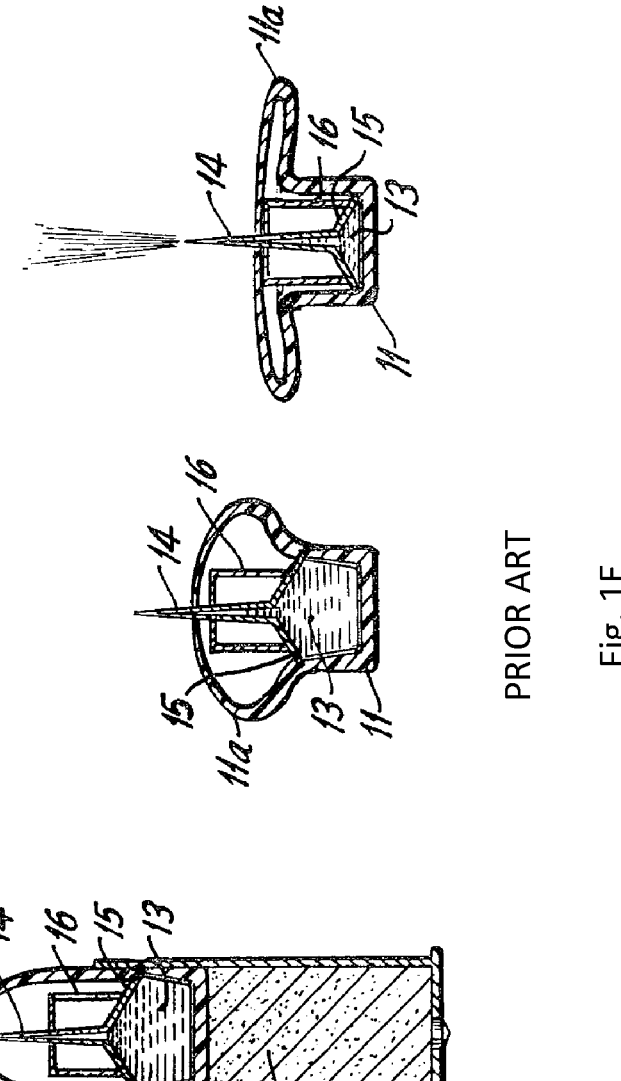

Many embodiments of the instant method and system for dosing a human or animal at a distance with a hypodermic formulation involve necessary interplay between medical and veterinary science, and external and terminal ballistics.

External ballistics entails the calculation, prediction, and performance of projectiles in-flight. Primarily, for the objective of dosing a human or animal with a hypodermic formulation, ballistic flight below approximately twenty-thousand feet altitude is germane; therefore, only "breathable atmosphere ballistic flight" will be considered and described. Terminal ballistics relates to the result or action a particular projectile has at the end of ballistic flight.

As defined herein, a "short-range ballistic distance" is less than 10 yards. As defined herein, a "medium-to-long range ballistic distance" is 10 to 100 yards. As defined herein, a "long range ballistic distance" is greater than 100 yards.

As defined herein, a "low ballistic velocity" is less than 300 feet per second. As defined herein, a "low-to-medium ballistic velocity" is 300 to 800 feet per second. As defined herein, a "medium-to-high ballistic velocity" is greater than 800 feet per second.

One cardinal rule of such ballistics related to solid projectiles is "the greater the mass, the greater the energy". This can be understood by exemplary Table 1. below of muzzle velocities and corresponding calculated muzzle energies (hereinafter, gr=grains, fps=feet per second, ft-lbs=foot pounds):

TABLE 1

| Mass | Velocity | Energy |
|---|---|---|
| 100 gr | 100 fps | 2 ft-lbs |
| 100 gr | 250 fps | 14 ft-lbs |
| 100 gr | 500 fps | 56 ft-lbs |
| 100 gr | 750 fps | 125 ft-lbs |
| 100 gr | 1000 fps | 222 ft-lbs |
| 100 gr | 1500 fps | 500 ft-lbs |
| 100 gr | 2000 fps | 888 ft-lbs |
| 100 gr | 2500 fps | 1388 ft-lbs |
| 100 gr | 3000 fps | 1998 ft-lbs |

However, many factors come into play when considering and discussing "lethal" ballistics. The U.S. Navy's Mark 45 cannon utilizes a five-inch diameter, seventy pound (approximately 500,000 gr) projectile imparting 435 ft-lbs of muzzle energy traveling at 20 fps; while a 9×19 mm 115 gr full metal jacketed bullet has a similar muzzle energy traveling at approximately 1,300 fps. At 20 fps the cannon shell would take several seconds to even exit the many foot-long barrel of the Mark 45, whereas the 9 mm projectile would exit a four-inch barrel at 3/10,000ths of a second. A person could quite literally dodge the massive Mark 45 shell at such a low velocity, if it exited the cannon muzzle at all. In fact, such a massive projectile would "fall out of the air" traveling at such a low velocity. In operational reality, the Mark 45 utilizes much higher muzzle velocities. Thus it can be appreciated and understood that the velocity of a projectile is not the entire story on lethality, nor is muzzle energy alone.

Additionally, terminal ballistics play a tremendous part in the story of projectile lethality. A projectile's shape, composition, configuration, and the like will and does greatly effect lethality.

Unless the projectile destroys the heart, lungs, or parts of the central nervous system (brain, spinal cord), it is quite possible that an individual or animal may survive a ballistic impact with modern and immediate trauma care. "Ballistic lethality" therefore is a variable concept in which it is virtually impossible to precisely predict whether or not a person or animal will die from any given projectile impact or wound.

Generally, the majority of lethal firearms propel a solid projectile at 800 feet per second (fps) or faster. The smallest, and often considered "the weakest of lethal rounds" is the commonly available .22 caliber short rim-fire. Subsonic, the twenty-two hundredths of an inch diameter thirty grain bullet travels at slightly faster than 800 fps imparting approximately 44 ft-lbs of muzzle energy. Such a configuration is indeed adequate to kill a human or animal, though typically not instantaneously. Conversely however, some have survived wounding from a 0.45 ACP ball round (200 gr, 900 fps, 360 ft-lbs), illustrating projectile lethality is not a cut-and-dry science nor art.

A further cardinal rule of external ballistics related to solid projectiles is "velocity and energy erode while mass remains constant". Notice in Table 1. above that the mass of the projectile did not change. At the end of flight striking nothing but atmosphere and after gravity and drag have taken their toll, the 100 gr projectile velocity and energy will return to zero as the projectile eventually strikes the ground. The projectile was 100 gr when fired, as it will be 100 gr when striking the ground, or a target. Hence, a primary goal of lethal external and terminal ballistics is to strike an intended living target before the velocity and energy for a given projectile fall below "assured lethal values".

Using simple to very complex calculations, standard tables can determine the overall "effective lethal range" of an unimpeded solid projectile, and the velocity and energy imparted when striking an object at any given point in ballistic flight.

In the realm of non-lethal weapons, the external ballistics of so-called air-guns or BB-guns has relevance. Professor Jim House, Adjunct Professor of Chemistry at Illinois Wesley University, discussed such in an essay entitled Airgun Ballistics, found at http://www.crosman.com/get-hunting/airgun-ballistics, and hereby incorporated in its entirety by reference.

Quoting Professor House, "A rifle chambered for the 0.22 long rifle cartridge fires a 40-grain bullet at approximately 1200 fps. A powerful .22 caliber air rifle . . . fires a 14.3 grain pellet with a muzzle velocity of approximately 900 fps. The firearm generates a muzzle energy of approximately 130 ft-lbs . . . whereas that of the air rifle is only about 26 ft-lbs. One frequently hears the expression describing an air rifle as "shoots as hard as a 0.22", but the firearm is much more powerful than any air rifle except perhaps some of the big bore 0.357 precharged pneumatics."

"In addition to the power factor, there is the difference in the trajectory of the projectile. Pellets used in air rifles do not have the aerodynamic efficiency of bullets used in firearms and, consequently, they lose velocity rapidly. Even the bullets used in 0.22 rim-fire rifles do not have the ability to penetrate air nearly as well as the streamlined bullets used in center fire rifles. The ability of a projectile to retain its velocity when passing through air is reflected by a variable known as the ballistic coefficient. The higher the ballistic coefficient, the less air resistance retards the motion of the projectile. For a relatively efficient .22 caliber pellet . . . , the ballistic coefficient is about 0.028, but the typical 40-grain bullet of a 0.22 long rifle cartridge has a ballistic coefficient of approximately 0.125. The result is that not only does a pellet fired from an air rifle have a muzzle velocity lower than that of even a bullet fired from a 0.22 rim-fire, it loses its velocity much more rapidly. All of this means that the path of the pellet involves a lot of curvature and it is more easily blown off course by wind.".

Another important factor in such calculations and performance is the rate of ballistic spin (that is, spiral rate or parabolic twist) of a projectile. So-called rifled muskets were invented in the 1700s and resulted in significant improvement in ballistic projectile performance, range, and accuracy.

And yet another important factor in eternal ballistics is the three axis center of gravity of a projectile. If a spiraling projectile is colloquially "tail heavy" or along the longitudinal axis is "out of round", the projectile may and will tumble in flight thus becoming less efficient and less accurate.

Another vital factor in such a system is the mass of the delivered and injected formulation. Typically, hypodermic formulations have the consistency and viscosity of water. A limiting aspect of known hypodermic delivery systems is "effective payload" due to formulation mass. Under sea-level and temperate conditions, water has the following volume to mass ratios: 1 ml=(0.9 grams or 13.8 grains); 2 ml=(1.9 grams or 29.3 grains); 3 ml=(2.8 grams or 43.2 grains); 4 ml=(3.8 grams or 58.7 grains); 5 ml=(4.9 grams or 75.6 grains); 10 ml=(9.6 grams or 148.1 grains); 15 ml=(14.5 grams or 223.8 grains); 20 ml=(19.3 grams or 297.8 grains); 30 ml=(28.9 grams or 445.9 grains). As can then be appreciated and understood, as the volume of a formulation payload increases, so does its mass and therefore the imparted energy to the recipient at ballistic flight termination.

Depending upon the formulation, it may be desired to inject a recipient with a high fluid volume hypodermic dosage and therefore a ballistically heavy projectile in and of itself. Add to the formulation the mass of the delivery system, and the risk of lethality of the system overall greatly increases.

It is therefore highly desired and an object of the instant inventive method and system to provide a hypodermic formulation delivery system capable of increased ballistic velocity during flight as compared to known methods and systems, by absorbing or redirecting the resulting increased imparted energy of the projectile away from the recipient upon impact, and correspondingly reducing the velocity and resulting imparted energy of the delivery system to less-than-lethal levels, thereby safely and effectively injecting the recipient with the formulation without causing serious physical harm to, nor the death of, the recipient.

Figure 2:
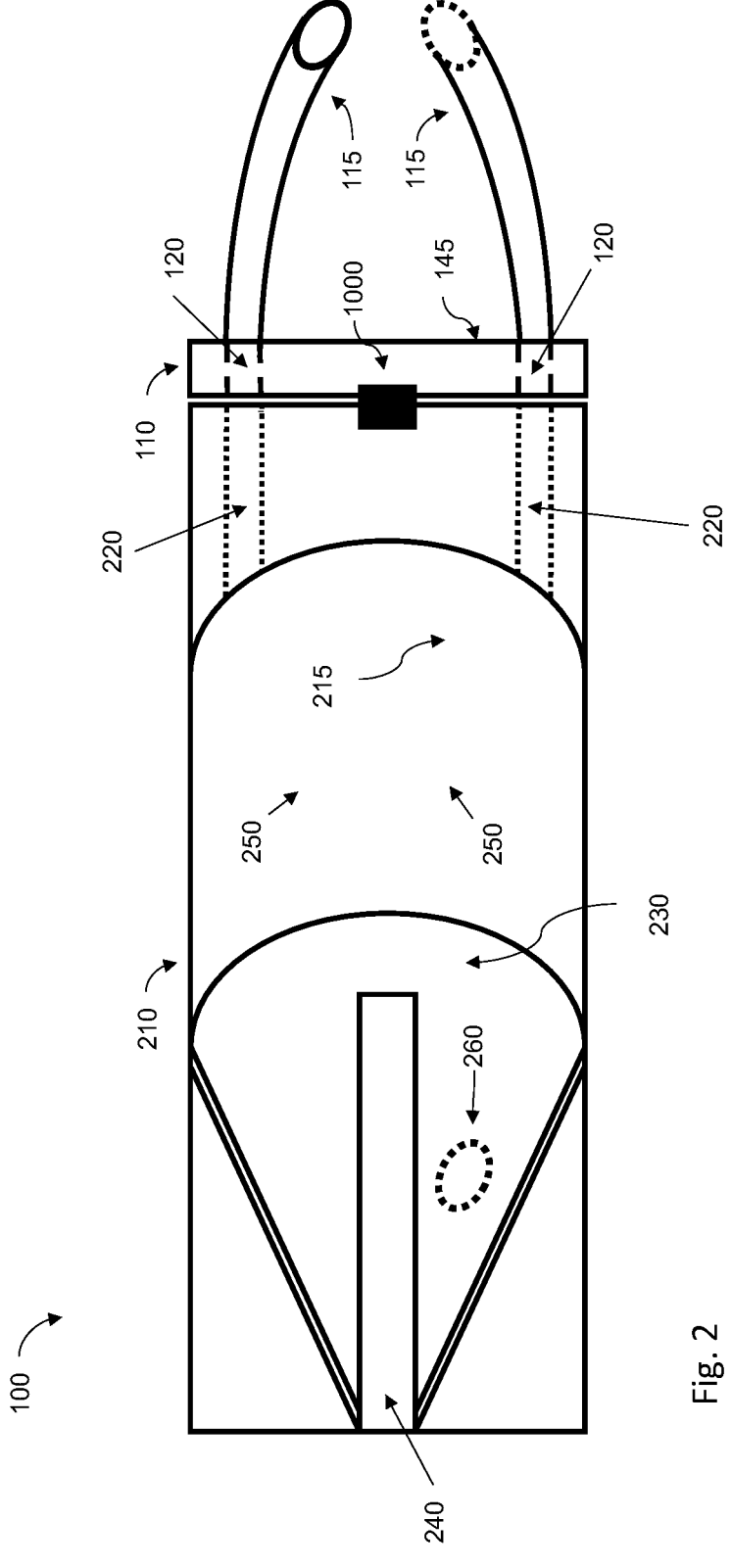
FIG. 2 is a schematic diagram of one embodiment of the projectile injection system.
Figure 3:
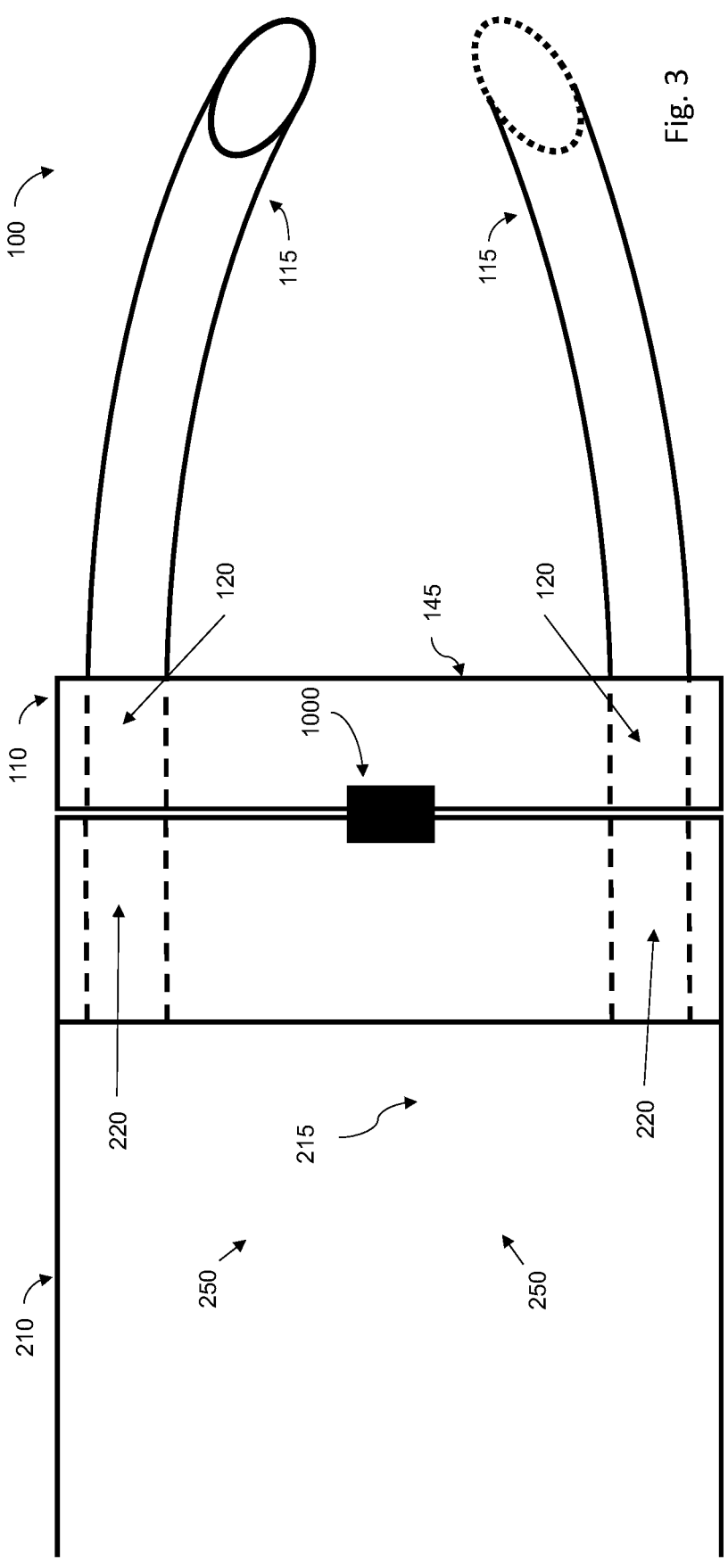
FIG. 3 is a schematic diagram of the embodiment of FIG. 2.
Figure 4:
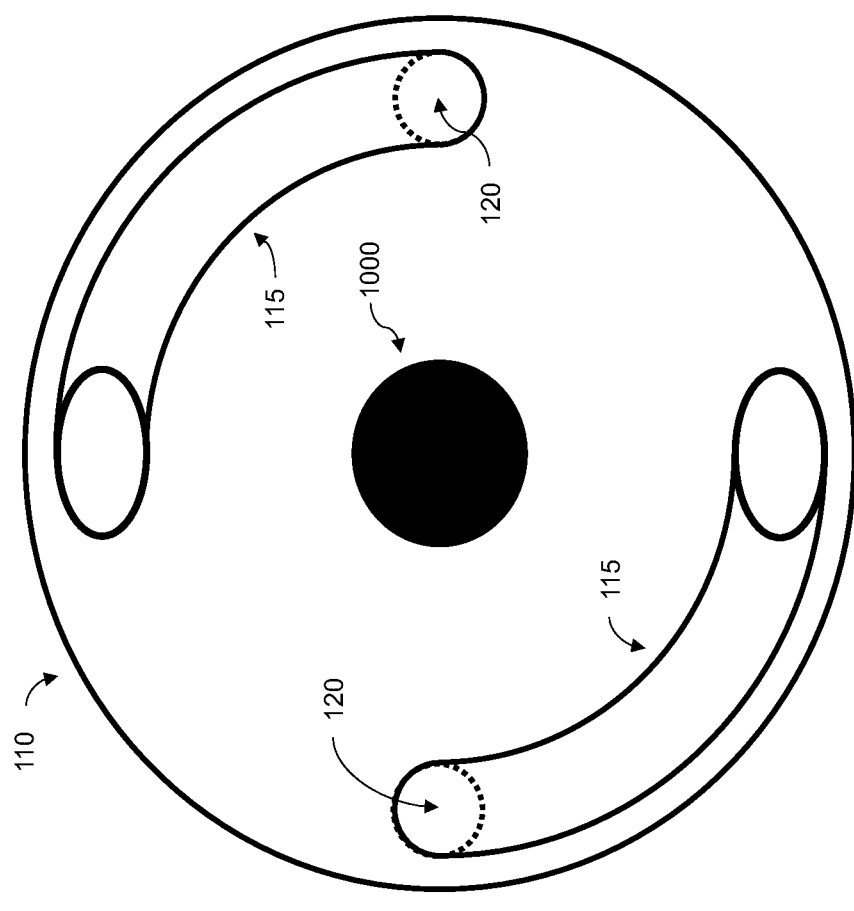
FIG. 4 is an end view of the embodiment of FIG. 2.

One embodiment of the instant inventive ballistic hypodermic formulation delivery system is depicted in FIG. 2. As depicted, the ballistic formulation delivery system 100 includes a ballistic injector head 110, a rotatable mount 1000, and a ballistic injector housing 210.

The injector housing 210 may include a cavity 215, an inertia activated plunger 230 internal to the housing, a medicative and/or sedative formulation 250, and one or more formulation collection or outlet port 220. In certain embodiments, the medicative and/or sedative formulation 250 is located within the cavity 215.

The injector head 110 may include one or more hypodermic needles 115 including one or more barb (not shown) to prevent dislodgement of the one or more hypodermic needles 115 from the recipient, and one or more formulation reception or inlet port(s) 120 which by intention and design compliment and utilize induced longitudinal and rotational inertial forces transferred to the hypodermic injector head 110 via the rotatable mount 1000 from the spinning injector housing 210 and the formulation 250 within the cavity 215, in order to safely and effectively penetrate the derma of the recipient with the at least one hypodermic needle, and to cause the injection of the medicative and/or sedative formulation 250 from the cavity 215 into the recipient.

In certain embodiments, one hypodermic needle 115 is contemplated, and in additional embodiments, two or three or more hypodermic needles are contemplated extending distally from the injector head 110.

In certain embodiments, the one or more hypodermic needles are curved or hooked extending distally from the injection head base approximately one-half to three inches. Relatedly, the diameter of the injector head would be commensurate with and vary depending upon the propulsion system used and the caliber of such system. By way of example, it is contemplated that the overall delivery system size and configuration is similar to and compatible with known firearms chambered in and for 0.410 thru 0.12 gauge shot-shells, and also for known 40 mm grenade or canister launcher rounds. It is further contemplated that the delivery system size and configuration be chambered in and compatible for use with known lethal revolvers and pistols such as but not limited to: .22 Long Rifle, 0.380 ACP, 9 mm Luger, 0.38 Special, 0.357 Magnum, 0.40 S&W, 10 mm Auto, 0.44 Special, 0.44 Magnum, 0.45 ACP, 0.50 Action Express, and 0.500 S&W Magnum.

Figure 7:
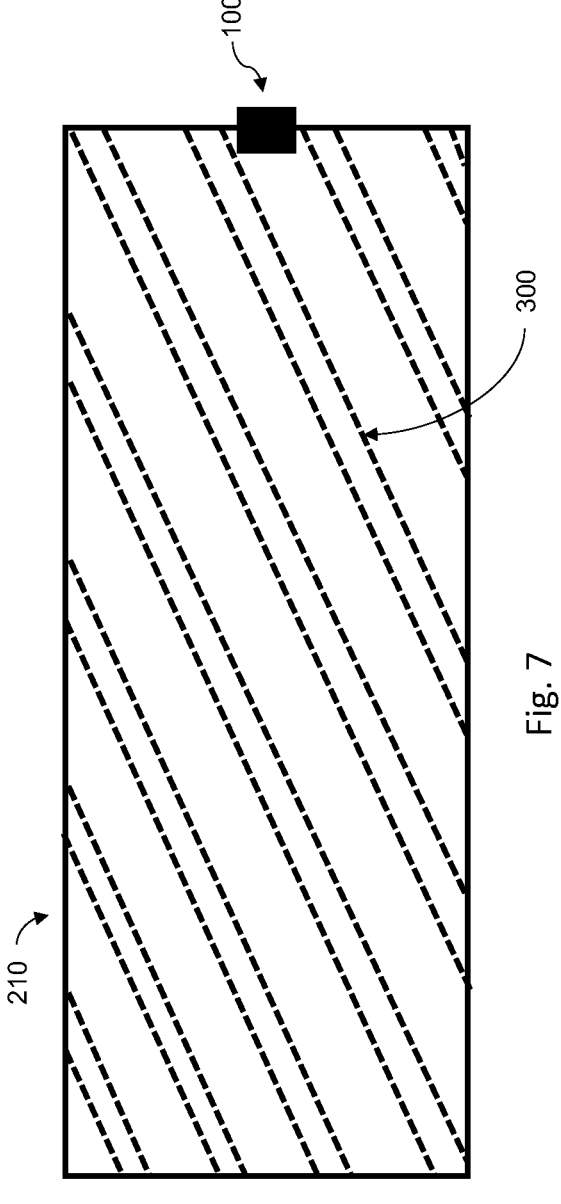
FIG. 7 is a schematic diagram of the housing of one embodiment of the projectile injection system.
Figure 8:
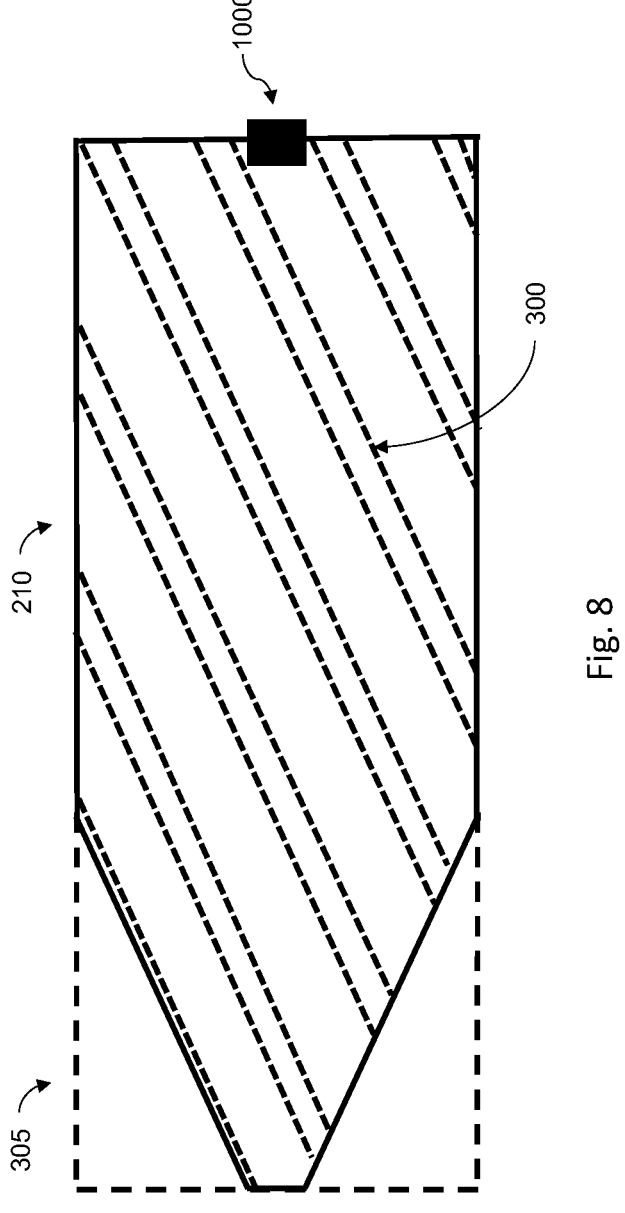
FIG. 8 is a schematic diagram of the housing of one embodiment of the projectile injection system.

One possible inventive embodiment basic theory of operation is as follows: delivery system 100 is propelled at low ballistic velocities ranging from 50 to 300 feet per second to a recipient. Preferably, by rifling on the ballistic injector housing 210 (FIGS. 7 and 8, Ref. No. 300), by offset aerodynamic fins or stabilizers (FIG. 8, Ref. No. 305), or by rifling inherent to the launcher or gun used (not shown); as the injector housing 210 spirals along a trajectory thus providing ballistic and gyroscopic stability to the housing 210, the rotatable mount 1000 transfers and/or induces a corresponding rotational spin to the injector head 110.

Depending on the system configuration, it is contemplated that the rotatable mount 1000 may freely spin or act as a clutch to induce a desired or specific rate of rotation or spin to the injector head 110. In this way, known and predetermined inertial forces may be used to "cooperatively twist or spiral" the at least one hypodermic needle 115 into the recipient facilitative of safe and effective subdermal bolus injection of the formulation 250.

It is also contemplated that the at least one hypodermic needle 115 is hooked or arced in a manner as and in order to "drill into" a recipient to a depth facilitative of safe and effective subdermal bolus injection, and to also constructively halt distal or forward movement, and also constructively halt rotation, upon the injector head base 145 impacting the recipient. Thus the housing 210 as allowed by the rotatable mount 1000 continues rotation and thereby transfers, converts, redirects, dissipates, or conveys any remaining kinetic energy by way of friction and heat to the rotatable mount 1000. In this way, the delivery system may realistically be propelled at and impact a living recipient at greater ballistic velocities and having a greater mass than as would a conventional and known projectile of similar mass lacking a rotatable mount 1000, thereby greatly reducing the potential lethality of the delivery system 100.

As depicted in FIGS. 3-6, preferably the at least one outlet port 220 is configured in such a way to be rotatably and yet be sealably in fluid communication with the at least one inlet port 120 in order to dose the recipient with the formulation 250 by way of the at least one hypodermic needle 115. This may be accomplished in a variety of known ways including but not limited to using O-ring seals, tongue and grove seals, precision face-to-face surfaces, or the like. Regardless of the rotation and/or sealing technology or configuration used, the injector housing 210 should rotate in relation to the injector head 110 while allowing for or facilitating the displacement of the hypodermic formulation 250 from the injector housing 210 cavity 215 to and through the injector head 110 and into the recipient upon or after the at least one hypodermic needle 115 penetrates the recipient.

Figure 5:
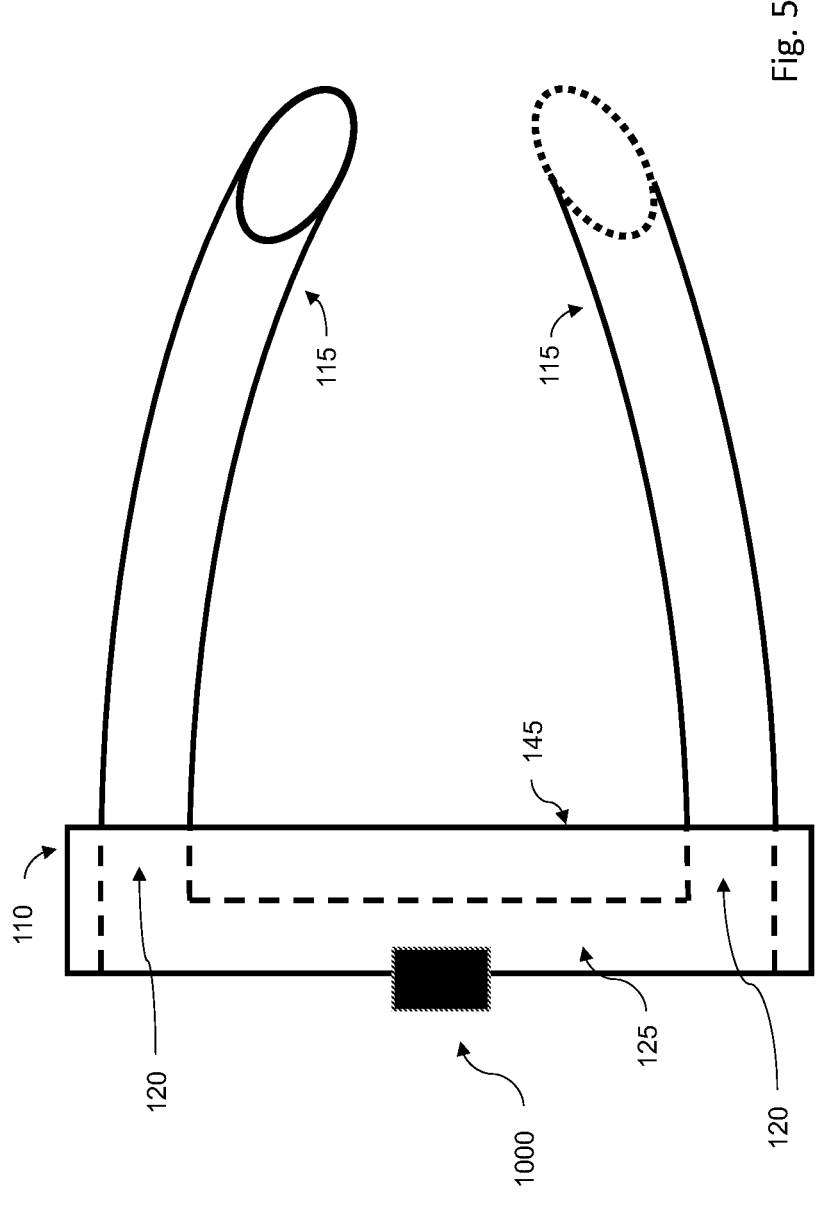
FIG. 5 is a schematic diagram of one embodiment of the inventive projectile injection system.
Figure 6:
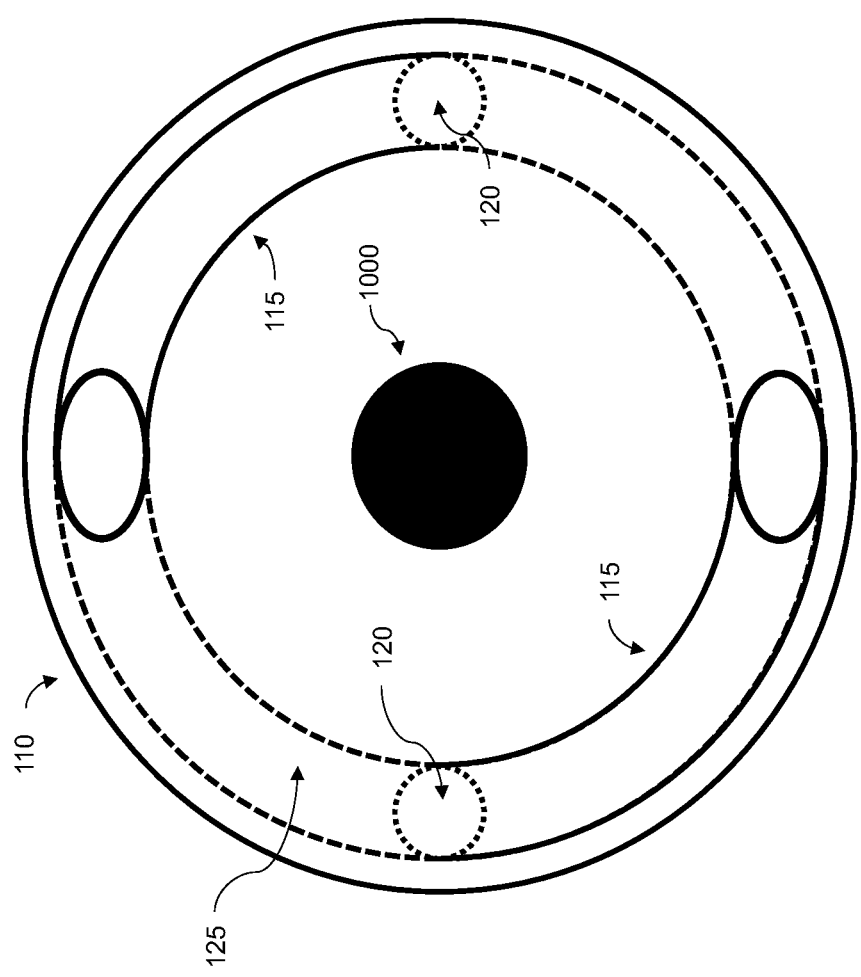
FIG. 6 is an end view of the embodiment of FIG. 5.

As depicted in FIGS. 5 and 6, another inventive embodiment includes a cooperative formulation reception channel or troth 125 in fluid communication with the at least one outlet port 220 and the at least one inlet port 120. Such a configuration allows for easier and more efficient sealing of the delivery system, allows for ease of rotation of the injection head 110, and therefore facilitate a greater rate of induction of the hypodermic formulation 250. As depicted in FIGS. 5 and 6, such a configuration allows for an increased flow of fluid into a recipient.

Figure 9:
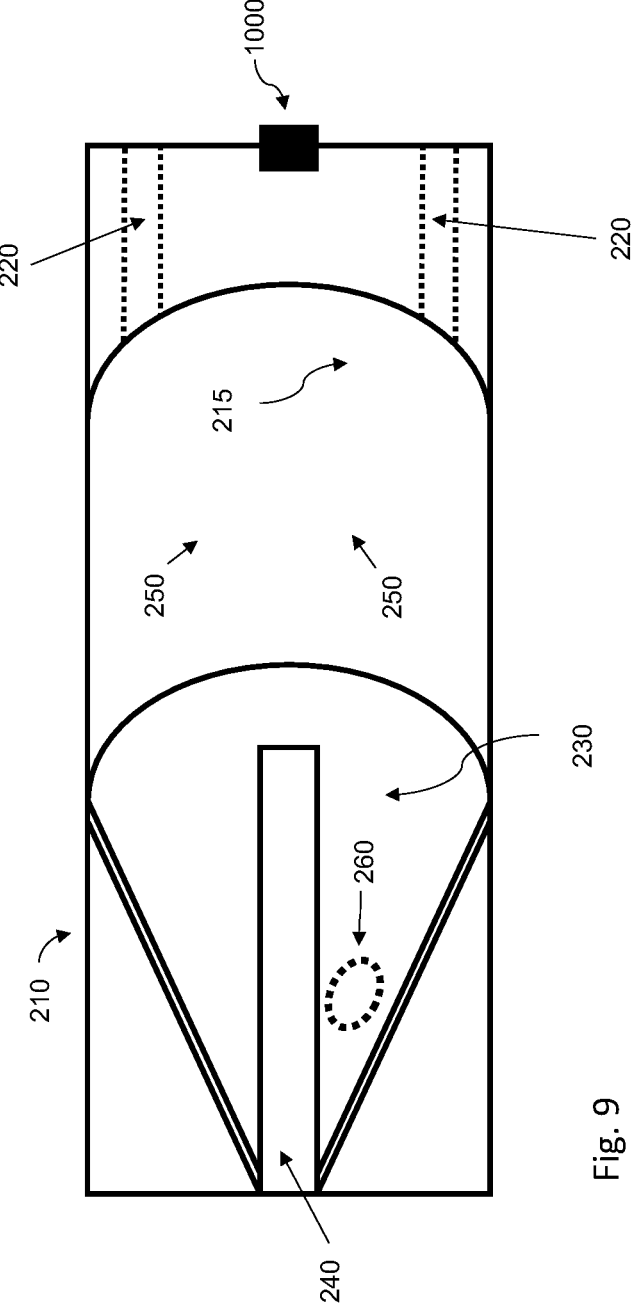
FIG. 9 is a schematic diagram of one embodiment of the projectile injection system in a first position.
Figure 10:
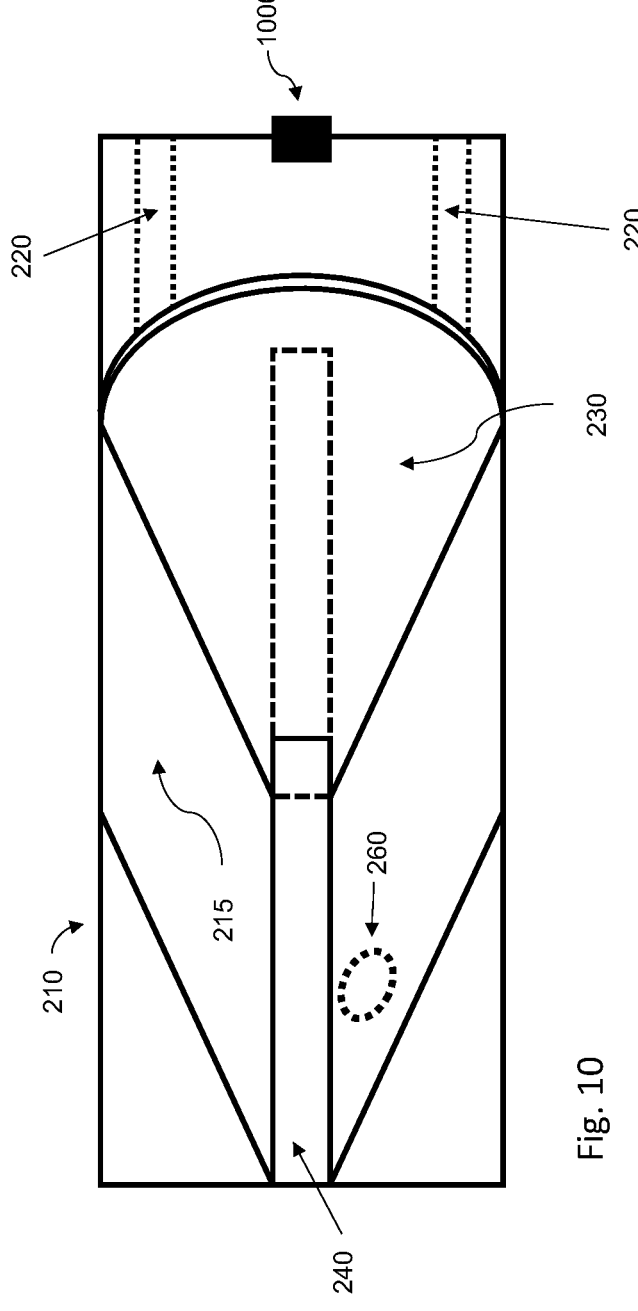
FIG. 10 is a schematic diagram of the embodiment of FIG. 9 in a second position.
Figure 11:
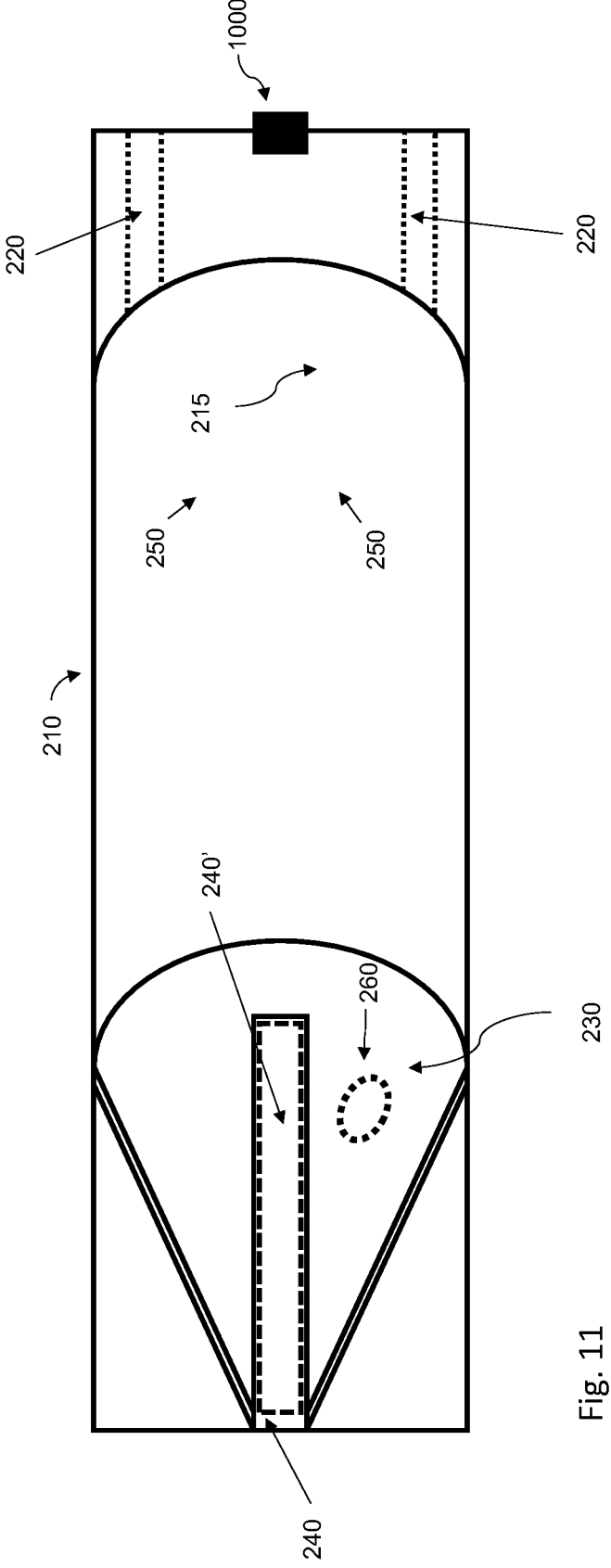
FIG. 11 is a schematic diagram of one embodiment of the projectile injection system in a first or proximal position.
Figure 12:
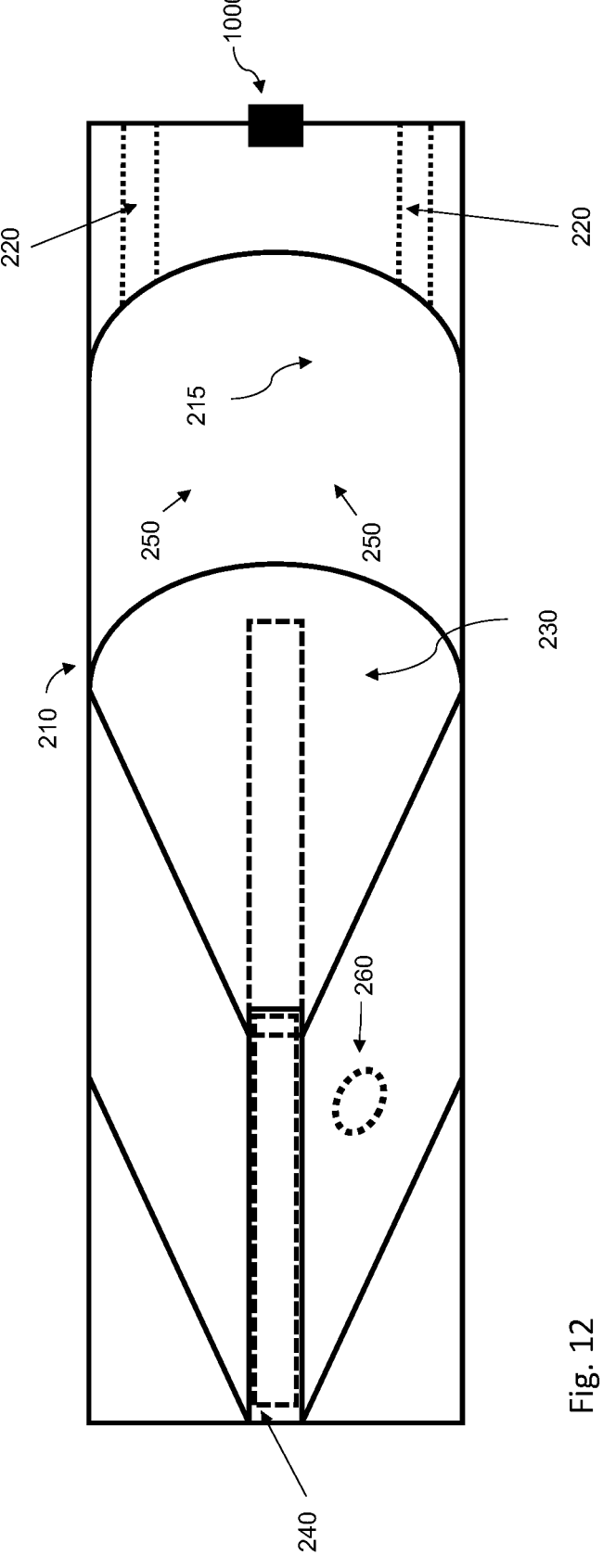
FIG. 12 is a schematic diagram of the embodiment of FIG. 11 in a second or intermediate position.
Figure 13:
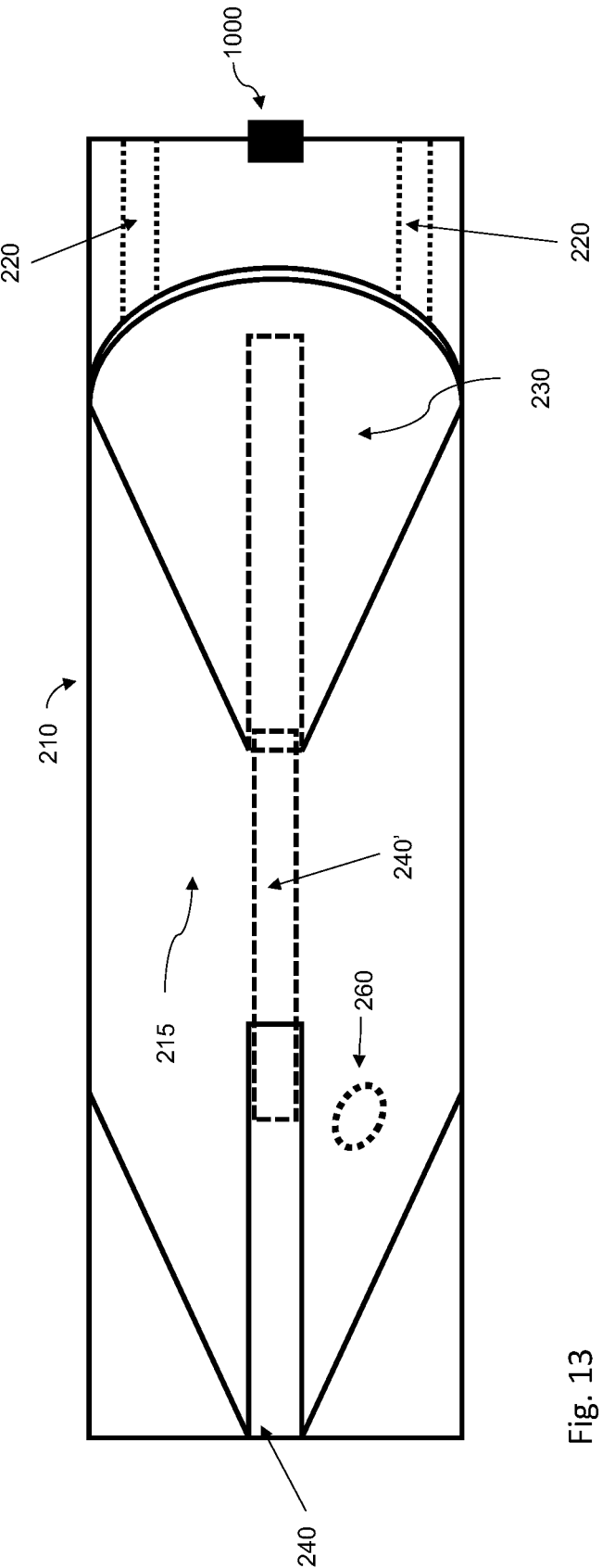
FIG. 13 is a schematic diagram of the embodiment of FIG. 11 in a third or distal position.

As depicted in FIGS. 9 and 10, another inventive embodiment of the housing 210 includes an inertial plunger 230, a centering post 240, and a housing vent 260. In accordance with Newton's first law of motion, when the delivery system 100 impacts a solid, semi-solid, or non-Newtonian fluid target, the inertial plunger 230 displaces distally toward the recipient resulting in the injection of the formulation 250. A housing vent 260 may be provided to prevent a vacuum from forming behind the plunger 230 and thus retarding, impeding, or preventing injection of the formulation 250. The vent 260 therefore allows for pressure equalization within the housing 210 and cavity 215 as the plunger 230 is displaced. Centering post 240 may be provided to guide and prevent the inertial plunger 230 from becoming cocked within the injector housing 210 and cavity 215 during displacement and hinder formulation 250 injection. As depicted in FIGS. 11, 12, and 13, a telescoping centering post 240' may also be provided depending upon length of the housing 210, and therefore the required "throw of" or "distance of displacement" of the plunger 230.

Figure 14:
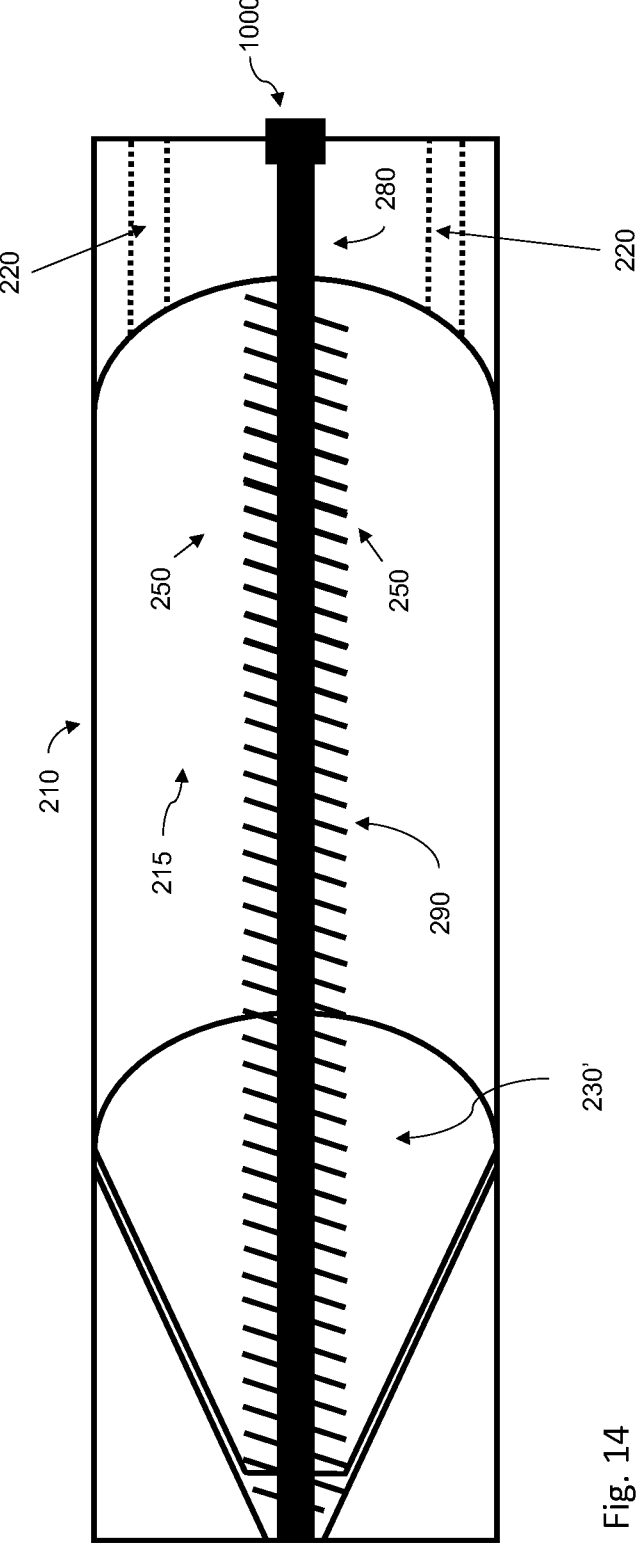
FIG. 14 is a schematic diagram of one embodiment of the projectile injection system in a first or proximal position.
Figure 15:
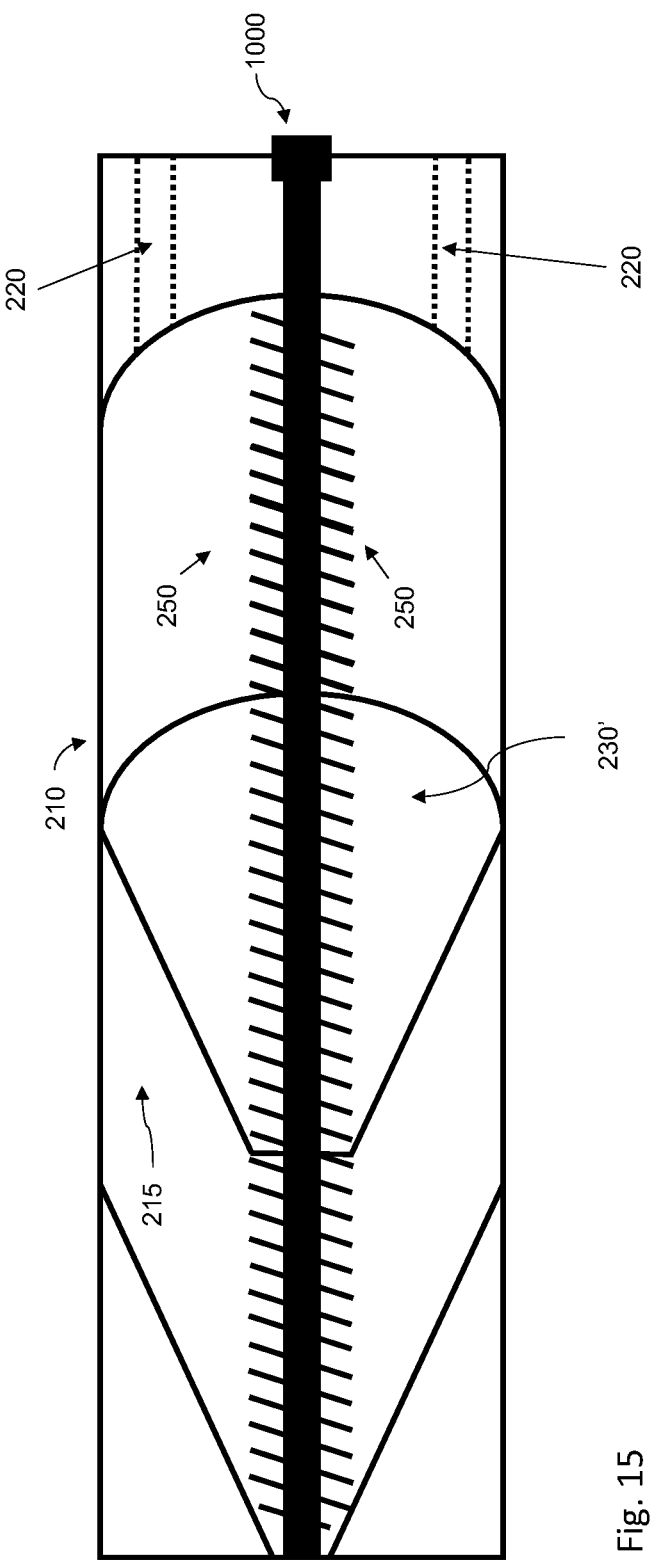
FIG. 15 is a schematic diagram of the embodiment of FIG. 14 in a second or intermediate position.
Figure 16:
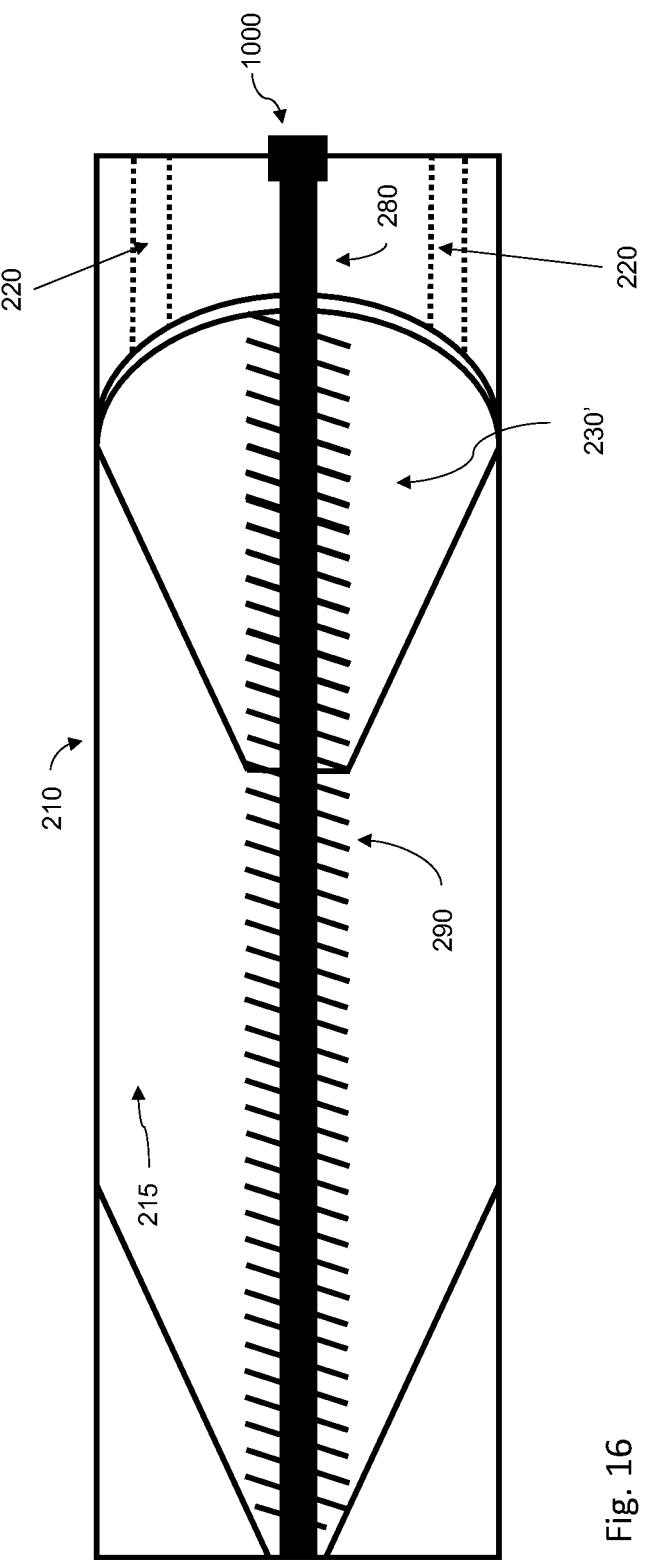
FIG. 16 is a schematic diagram of the embodiment of FIG. 14 in a third or distal position.

As depicted in FIGS. 14, 15, and 16, another inventive embodiment of the housing 210 includes a plunger 230', a shaft 280, and a worm gear 290 in communication with the plunger 230'. In operation, it is contemplated that the shaft 280 is in mechanical communication with either the rotatable mount 1000 and/or the injector head 110, and is allowed to rotate within the injector housing 210. Thereby, when the injector head 110 halts rotation upon impacting a recipient, the injector housing 210 cooperatively continues to rotate about the shaft 280 and the worm gear 290, thus displacing the plunger 230' along the longitudinal axis of the housing resulting in the injection of the formulation 250.

Figure 17:
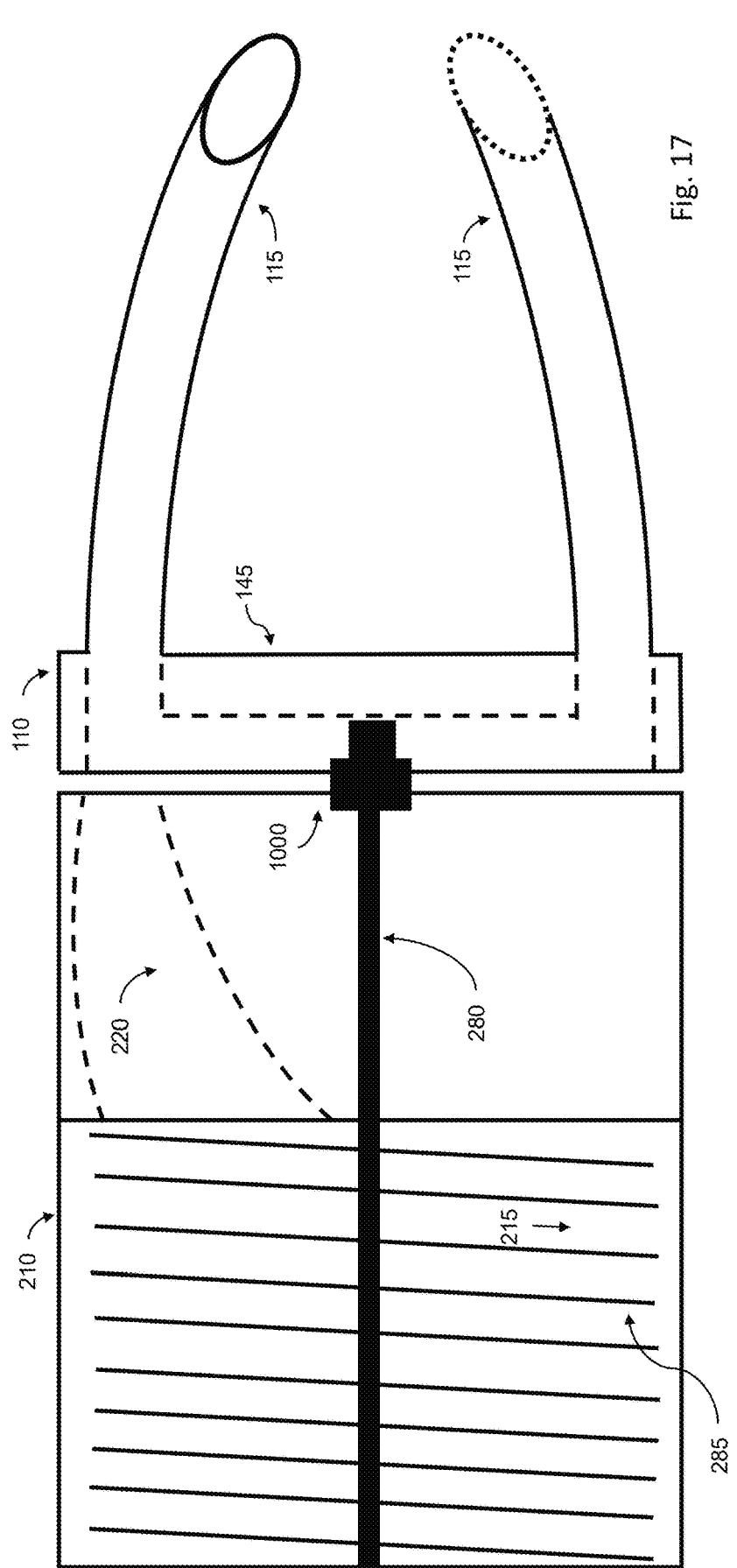
FIG. 17 is a schematic diagram of one embodiment of the projectile injection system in a first position.
Figure 18:
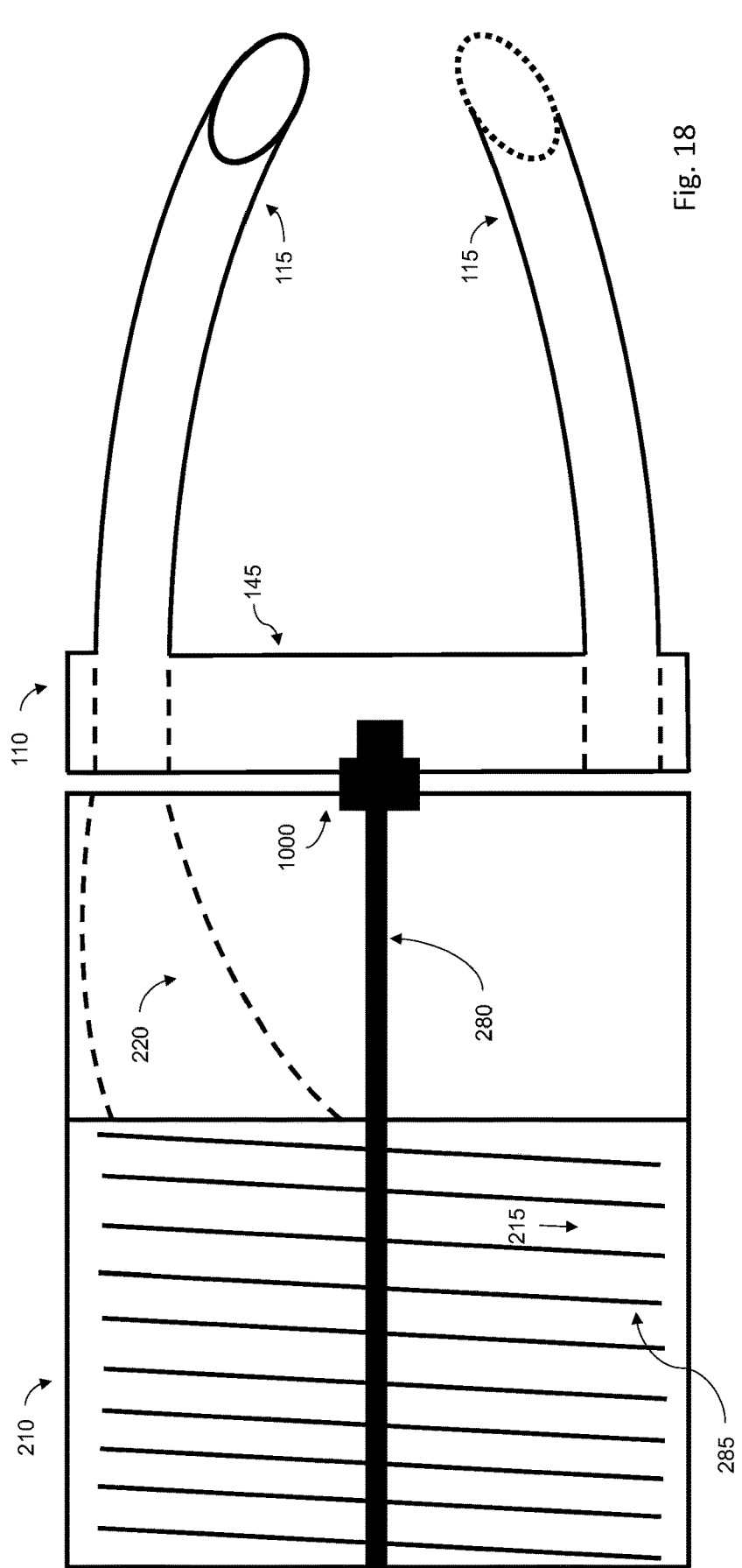
FIG. 18 is a schematic diagram of one embodiment of the projectile injection system.
Figure 19:
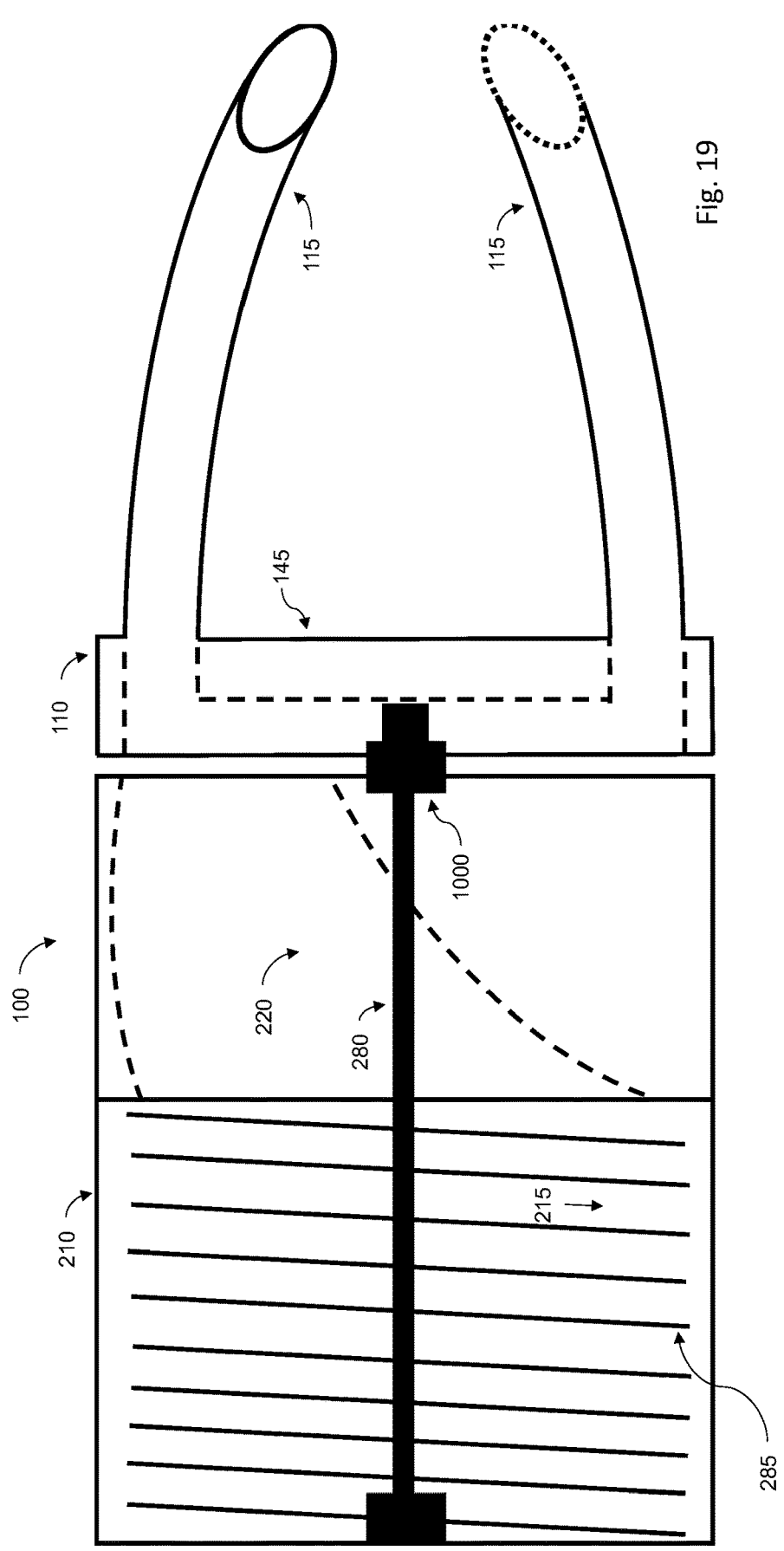
FIG. 19 is a schematic diagram of the embodiment of FIG. 17 in a second position.

As depicted in FIGS. 17, 18 and 19, another inventive embodiment of the housing 210 includes a turbine or corkscrew palate 285 and a shaft 280 in mechanical communication with either the rotatable mount 1000 and/or the injector head 110, and allowed to rotate free of and within the injector housing 210. Thereby, when the injector head 110 halts rotation upon impacting a recipient, the injector housing 210 continues to rotate about the shaft 280 and the turbine or corkscrew palate 285 forces the formulation into the at least one outlet port 220, and resulting in the injection of the formulation 250.

What is highly desired and an object of the instant inventive method and system is to provide a hypodermic delivery system capable of dosing a recipient with a formulation having a combined mass between 10 and 500 grains, propelled at low-to-medium ballistic velocities (300 to 800 fps) and with medium-to-long range ballistic accuracy (10 to 100+ yards) without causing serious physical harm to, nor the death of, the recipient.

This objective may be accomplished using a staged or graceful velocity degradation method and system. All known systems utilize a single method or stage of reducing imparted energy of known non-lethal projectiles.

Typically, a collapsible or deformable material is added to the distal or forward nose of a projectile. As the projectile impacts a recipient the material deforms whereby the projectile velocity is reduced and the energy imparted is dissipated over a wider impact area in hopes of not seriously injuring or killing the recipient. Brydges-Price '810, Brydges-Price '908, Baltos, Delphia, and Muller referenced and discussed earlier all utilize such collapsing or deforming material energy absorbing method and system. However, using such impact reducing material alone is largely inadequate to prevent serious harm to or death of a recipient when impacted by projectiles traveling above 300 fps, regardless of projectile mass.

Therefore, by using such known energy absorbing materials with the instant inventive hypodermic formulation delivery system 100 including a rotatable mount 1000, higher ballistic velocities may be realized thus improving the performance, range, and accuracy of non-lethal projectiles and systems.

Further and accordingly, the instant inventive delivery system 100 may also include a forward of or leading-edge airfoil. In this regard, the inventions and work of the late Abraham Flatau have relevance. Mr. Flatau was a pioneer in the fields of external and terminal ballistics, and later in life devoted his time and energy to designing and patenting novel aerial toys. One such is taught by U.S. Pat. No. 6,454,623 granted Sep. 24, 2002, (herein "Flatau" and included in its entirety by reference). Flatau includes a closely spaced colinearly aligned ring wing or airfoil connected by spokes to a central slender member. The instant inventive delivery system 100 may further comprise such an airfoil thus providing an additional stage of graceful velocity degradation when the instant inventive delivery system 100 strikes a recipient, as well as increasing the overall ballistic stability and performance of the instant inventive delivery system 100 in flight. An additional ballistic advantage to such a leading ring wing or airfoil configuration is that depending upon the airfoil configuration, a partial vacuum may be created within and behind the airfoil via a venturi effect. The central slender member of Flatau encounters reduced aerodynamic drag due to its placement central to and within the ring wing or airfoil. This induced venturi effect may be utilized to further reduce the aerodynamic drag, and thus increase the velocity of the instant inventive housing 210 and injector head 110 when similarly configured.

As depicted in FIGS. 20A-20E, an inventive embodiment of the injector head 110 includes a ring wing or airfoil 400 distal to, forward of, or leading the injector head 110, and releasably in mechanical communication with the injector head 110 by at least two or more spokes 410.

Figure 20A:
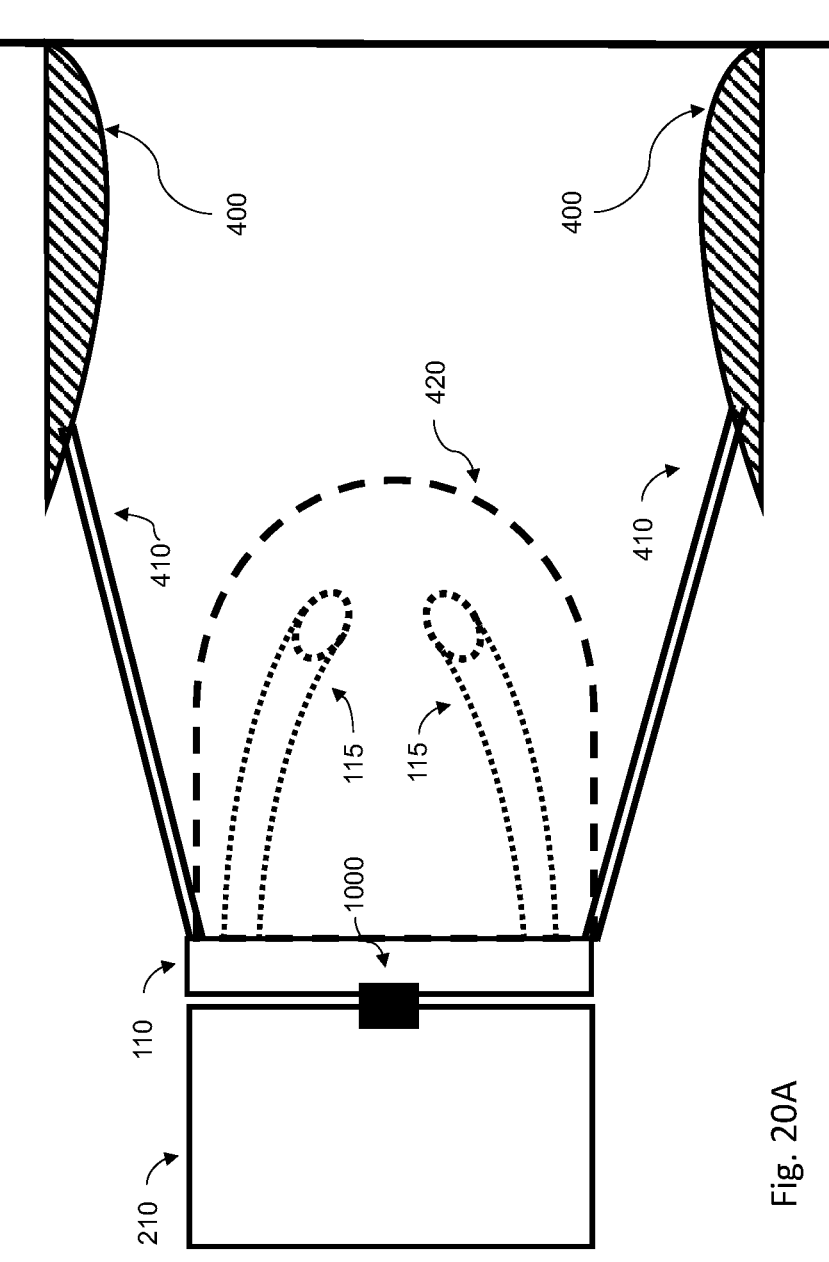
FIGS. 20A-20F are schematic diagrams of one embodiment of the projectile injection system.
Figure 20B:
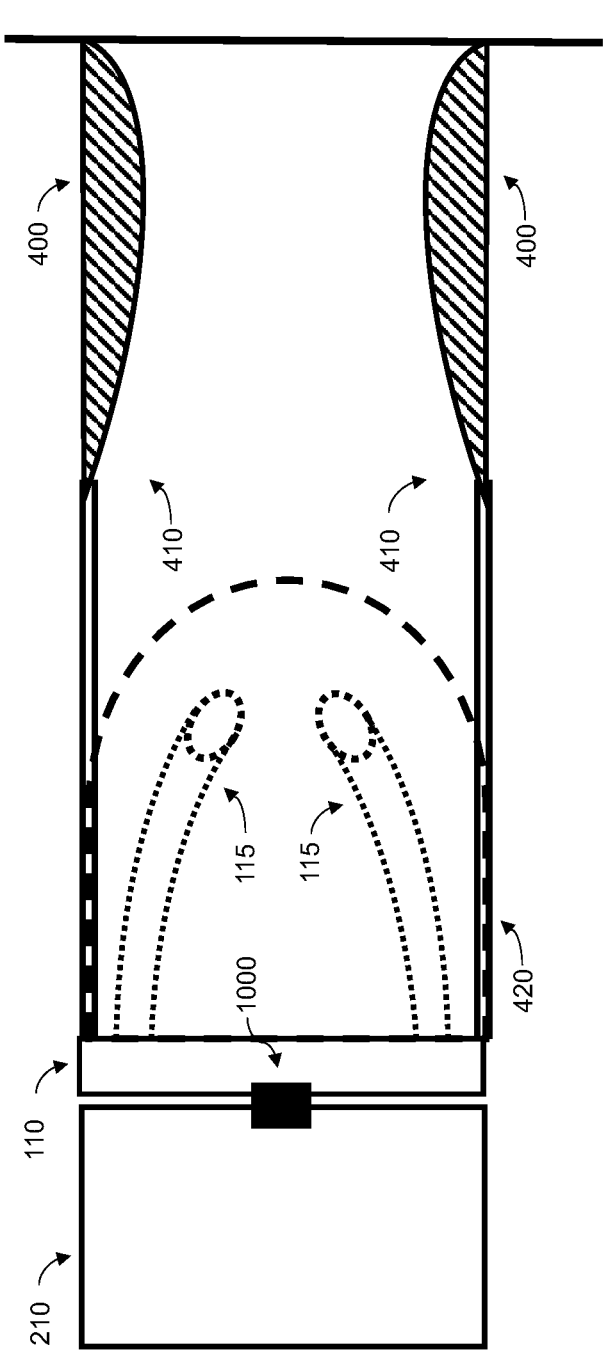

As depicted in FIG. 20A, it is contemplated that a ring wing or airfoil 400 may be capable of expanding in outer circumference greater than the outer circumference of either the housing 210, the injector head 110, or both. After leaving a launcher or gun barrel muzzle, such expansion of the airfoil may be achieved by telescopic or expanding surface design and utilizing forces inherent to a spiraling ballistic projectile. Optionally, as depicted in FIG. 20B, the outer circumference of the ring wing or airfoil 400 may remain fixed throughout ballistic flight; as will be the case in the following explanative discussion.

As depicted and contemplated, a possible basic theory of operation for one such embodiment of the instant inventive delivery system 100, utilizing such a staged or graceful velocity degradation configuration, is as follows: As depicted in FIG. 20B, the delivery system 100 is propelled at low-to-moderate ballistic velocities up to approximately 800 fps. Preferably the delivery system 100 is caused to spiral in flight, either by rifling on the injector housing 210 (FIGS. 7 and 8, Ref. No. 300), by rifling on the outer surface of the ring wing or airfoil 400 (not shown), by offset aerodynamic stabilizers (FIG. 8, Ref. No. 305), or by rifling inherent to the launcher or gun barrel used (not shown). The spiraling provided by a launcher or gun barrel to the delivery system 100 directly or causationally imparts gyroscopic stability to the housing 210, the injector head 110, and/or the ring wing or airfoil 400.

Figure 20C:
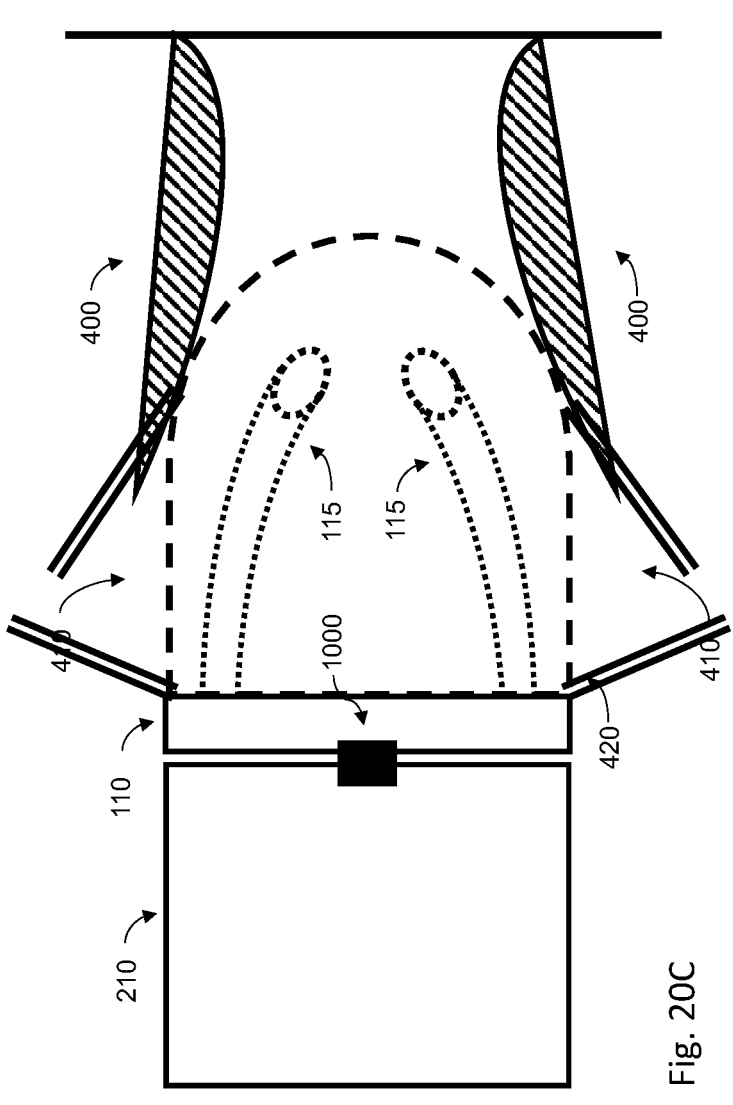

As depicted in FIG. 20C, upon the ring wing or airfoil 400 impacting a recipient 500, the at least two or more spokes 410 fracture, detach, or disengage from the injector head 110 and/or ring wing or airfoil 400 and thereby absorb, dissipate, or redirect a portion of the overall delivery system 100 velocity and resulting energy. It is contemplated that the ring wing or airfoil 400 have as little mass as possible, as to not cause serious harm to or the death of the recipient 500 upon impact. It is also contemplated that the ring wing or airfoil 400 be designed in such a manner as to segment, fracture, separate, and/or displace upon impact with the recipient 500 to further absorb or dissipate an increased portion of the overall imparted energy of the delivery system 100.

Figure 20D:
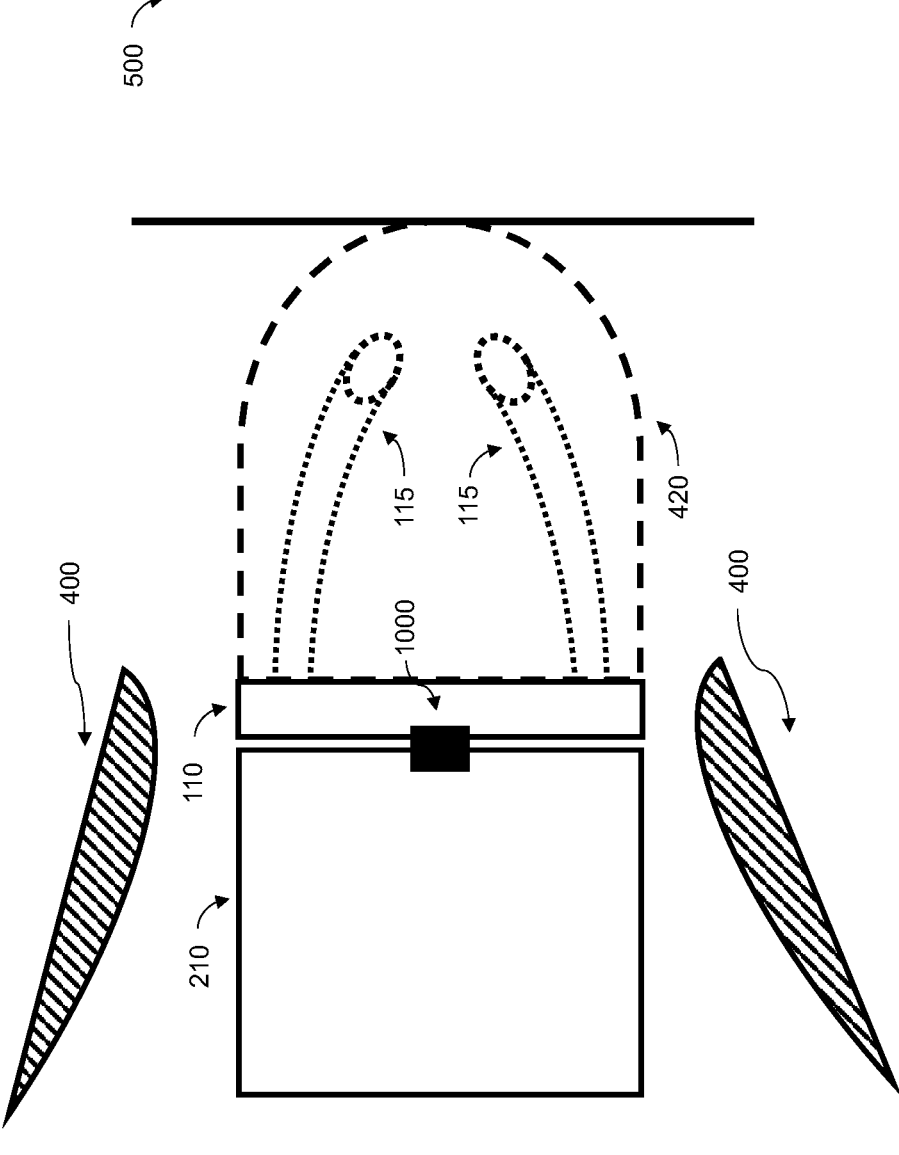

As depicted in FIG. 20D, once the injector head 110 has been slowed by and is free of the ring wing or airfoil 400, an energy absorbing nose cone 420 forward of or distal to the at least one hypodermic needle 115 next impacts the recipient 500 at a slower velocity than that of the ring wing or airfoil 400 leading edge. As the nose cone 420 either collapses, displaces, distorts, compacts, fractures, or detaches from the injector head 110, it thereby absorbs, dissipates, or redirects a further portion of the overall delivery system 100 velocity and imparted energy. It is contemplated that the rotatable mount 1000 may freely spin or act as a clutch to induce a desired or specific rate of rotation or spin to the injector head 110. In this way, known and predetermined inertial and ballistic forces may next be used to "cooperatively twist or spiral" the at least one hypodermic needle 115 into the recipient 500 facilitative of and for safe and effective subdermal bolus injection of the formulation 250; and further absorbing, dissipating, or redirecting a portion of the overall delivery system 100 imparted energy.

Figure 20E:
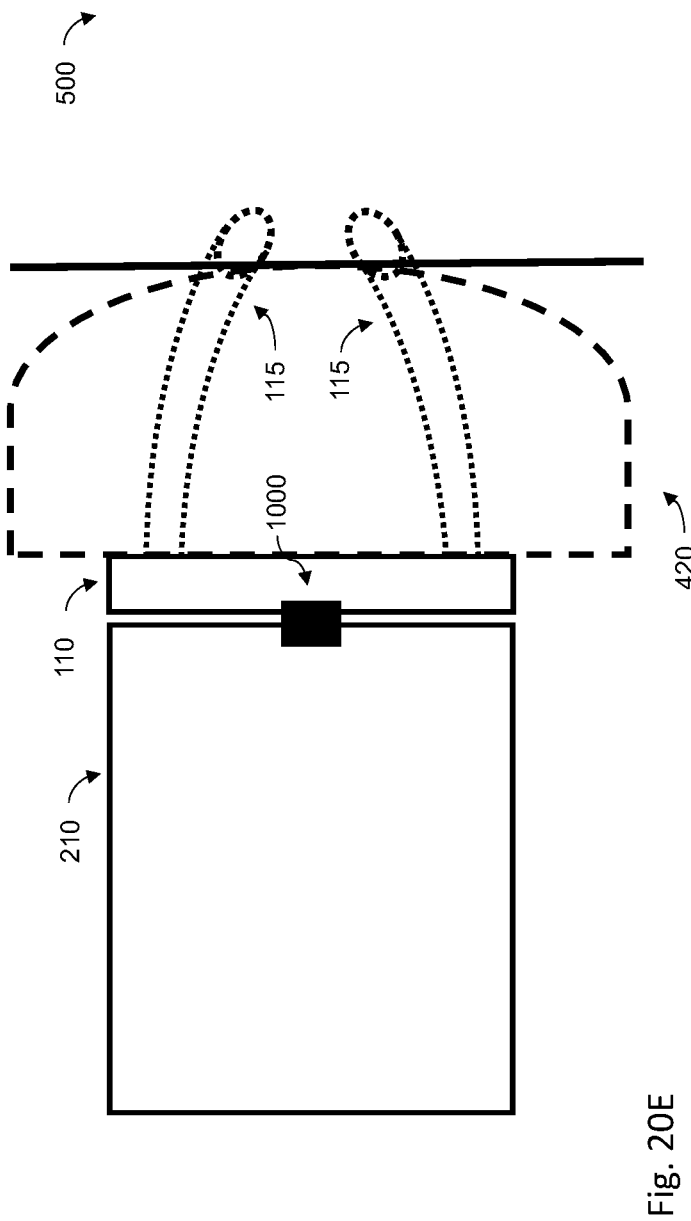
Figure 20F:
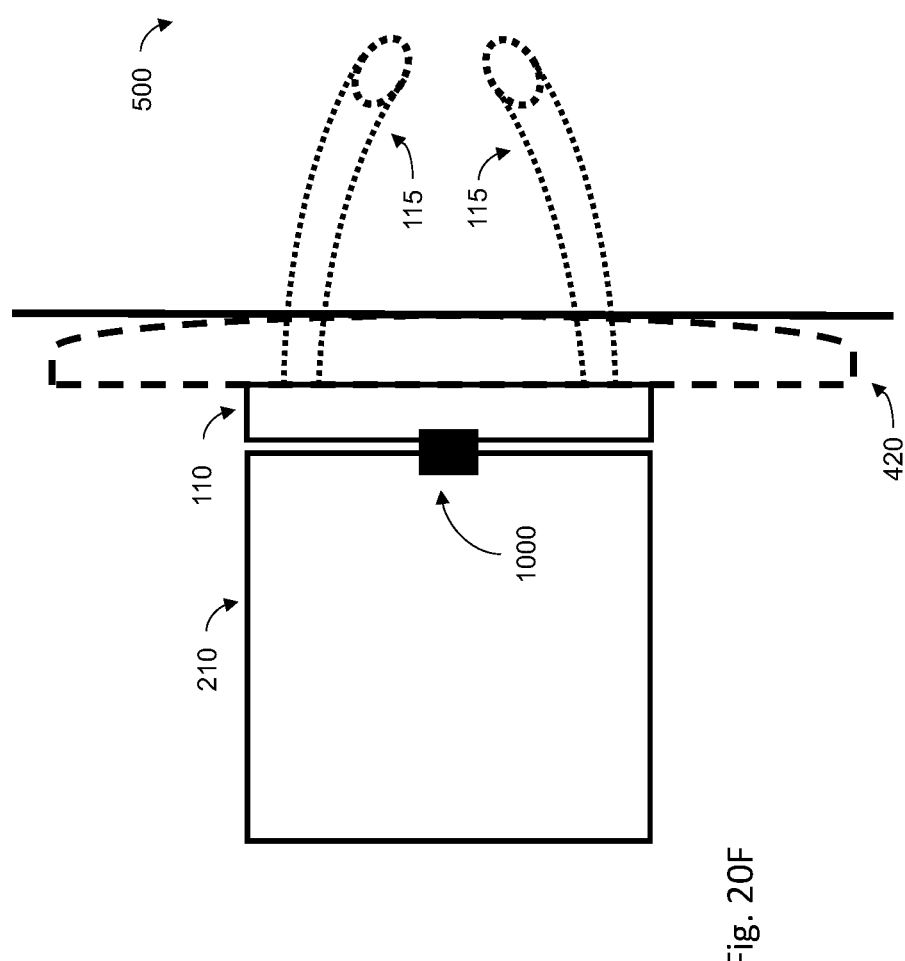

As depicted in FIG. 20E, it is also contemplated that the at least one hypodermic needle 115 is hooked or arced in order and as to "drill into" a recipient 500 to a depth facilitative of safe and effective subdermal bolus injection, and to also constructively halt distal or forward movement, and also constructively halt rotation, upon the injector head base 145 impacting the recipient 500. As depicted in FIG. 20E, thus housing 210 via the rotatable mount 1000 continues rotation and thereby transfers, converts, redirects, dissipates, or conveys the remaining portion of the imparted energy by way of friction and heat to the rotatable mount 1000. In this way, the delivery system may realistically be propelled at and impact a living recipient 500 at greater ballistic velocities and having a greater mass than as would a known conventional projectile of similar mass lacking the rotatable mount 1000, lacking the nose cone 420, and/or lacking the leading ring wing or airfoil 400.

The inventive method and system provides a delivery system adapted for dosing a recipient hypodermically with a formulation at a distance; the delivery system utilizing known common revolver, pistol, shot-gun, rifle, other fire-arms, and/or known launchers.

Additionally, many and varied known lethal weapons may utilize the inventive ballistic formulation hypodermic delivery system, such as but not limited to, single-shot, semi-automatic, or fully-automatic revolvers, pistols, shotguns, scatterguns, rifles, and combinations thereof.

Accordingly, the instant inventive method and system is not to be limited by the embodiments as described and depicted, as these are given by way of example only and not by way of limitation.

Having thus described several embodiments for practicing the inventive method and system, its advantages and objectives can be easily understood. Variations from the description above may and can be made by one skilled in the art without departing from the scope of the invention, which is to be determined from and by the following claims.

What is claimed is:

1. A spiraling ballistic flight projectile injection system for dosing a human or animal recipient with a formulation via injection at a ballistic distance, the system comprising:

a housing having a longitudinal axis, a distal end, and a proximal end, wherein said housing has at least one cavity storing the formulation and at least one distal outlet port through which the formulation exits said housing;

an injector head having a distal end, a proximal end, and a longitudinal axis in common with the housing longitudinal axis, including at least one proximal inlet port fluidly connected to the at least one distal outlet port of the housing, and including at least one curved distal hypodermic needle extending distally from the injector head offset from the housing and injector head longitudinal axis, the injector head proximal end mounted to the housing distal end along the housing and injector head longitudinal axis via a rotatable hub, the rotatable hub configured to allow the injector head to spin along the common longitudinal axis in respect to the housing, and wherein upon spiraling ballistic contact with the recipient, the at least one curved distal hypodermic needle, cooperatively with the direction of rotation of the housing and injector head along the common longitudinal axis of the housing and injector head, penetrates the dermis of the recipient to a depth facilitative of and suitable for subdermal bolus injection of the formulation, wherein the injector head when impacting the recipient constructively stops both distal and rotational movement along the common longitudinal axis, wherein the formulation exits the at least one cavity and passes through the at least one distal outlet port of the housing into the at least one proximal inlet port of the injector head and through the at least one curved distal hypodermic needle, so that the recipient is injected with the formulation without causing serious injury to or the death of the recipient.

2. The system of claim 1, wherein said projectile injection system is propelled by the group consisting of single-shot, semi-automatic, or fully automatic revolvers, pistols, shotguns, scatterguns, rifles, and combinations thereof.

3. The system of claim 1, wherein the housing further includes a plunger and a housing vent, wherein the housing vent allows for housing pressure equalization when and as the plunger displaces resulting in the injection of the formulation into the recipient.

4. The system of claim 1, wherein the injection system comprises a turbine or worm gear in communication with the rotatable hub, wherein when the housing continues rotation as the injector head remains constructively stationary, the turbine or worm gear forces the formulation through the at least one outlet port resulting in the injection of the formulation into the recipient.

5. The system of claim 1, wherein the system is reusable.

6. The system of claim 1, wherein the injector system utilizes inertial forces upon impact of the injector head with the recipient resulting in the injection of the formulation into the recipient.

7. The system of claim 4, wherein the housing further includes a worm gear along the common longitudinal axis in communication with the plunger and in communication with the rotatable hub, whereby the continuing rotation of the housing along the common longitudinal axis in relation to the hypodermic injector head and after impact with the recipient causes the plunger to displace along the common longitudinal axis resulting in the injection of the formulation.

8. The system of claim 4, wherein the housing further includes a gas under pressure, wherein when the gas is suddenly released, or comprises an explosive substance whereby when ignited expands, or comprises a spring under compression whereby when suddenly released, causes the plunger to displace resulting in the injection of the formulation.

9. The system of claim 1, wherein the at least one hypodermic needle further includes a barb.

10. The system of claim 1, wherein the at least one hypodermic needle is configured in an arc.

11. The system of claim 10, wherein the at least one hypodermic needle is configured in one or more cycloidal, epicycloidal, hypocycloidal, or other spiral arc.

12. The system of claim 1, wherein the injector head further comprises at least one cooperative strut corresponding to the at least one hypodermic needle and configured in such a manner as to facilitate dermal penetration of the recipient by the at least one hypodermic needle and to facilitate the injection of the formulation into the recipient.

13. The system of claim 1, wherein the outer circumference of the projectile injection system changes during ballistic flight.

14. The system of claim 1, wherein the outer circumference of the projectile injection system changes after impacting the recipient.

15. The system of claim 1, wherein the rotatable hub further includes or operates as a clutch between the housing and the injector head.

16. The system of claim 1, wherein the injector head further includes an airfoil.

* * * * *